United States Patent
Kasahara et al.

[11] Patent Number: 5,847,005
[45] Date of Patent: Dec. 8, 1998

[54] BENZAMIDOXIME DERIVATIVES, PROCESS PRODUCTION THEREOF, AND AGROHORTICULTURAL BACTERICIDE

[75] Inventors: Isamu Kasahara; Hirohito Ooka; Shinsuke Sano, all of Kanagawa; Hiroyasu Hosokawa; Homare Yamanaka, both of Shizuoka, all of Japan

[73] Assignee: Nippon Soda Co., Ltd., Tokyo, Japan

[21] Appl. No.: 849,811

[22] PCT Filed: Dec. 18, 1995

[86] PCT No.: PCT/JP95/02596

§ 371 Date: Aug. 14, 1997

§ 102(e) Date: Aug. 14, 1997

[87] PCT Pub. No.: WO96/19442

PCT Pub. Date: Jun. 27, 1996

[30] Foreign Application Priority Data

Dec. 19, 1994 [JP] Japan .................................... 6-334497
May 19, 1995 [JP] Japan .................................... 7-145502

[51] Int. Cl.$^6$ .......................... A01N 37/18; C07C 233/05
[52] U.S. Cl. .......................... 514/617; 514/523; 514/538; 514/539; 514/616; 558/391; 558/392; 560/39; 560/41; 564/152; 564/154; 564/155; 564/157; 564/158; 564/161; 564/170
[58] Field of Search .................................... 514/616, 617, 514/523, 538, 539; 564/142, 161, 162, 163, 164, 165, 166, 168, 152, 154, 155, 157, 158, 170; 558/391, 392; 560/39, 41

[56] References Cited

U.S. PATENT DOCUMENTS 5,112,382  5/1992  Hsu ............................................ 71/88

FOREIGN PATENT DOCUMENTS 2-6453 A  1/1990  Japan .

*Primary Examiner*—Shailendra Kumar
*Attorney, Agent, or Firm*—Jacobson, Price, Holman & Stern, PLLC

[57] ABSTRACT

The present invention relates to benzamidoxime derivatives represented by the formula [I];

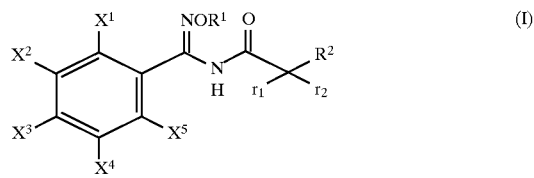

wherein $R^1$ is unsubstituted or substituted $C_1$–$C_4$ alkyl, unsubstituted or substituted $C_2$–$C_4$ alkenyl or unsubstituted or substituted $C_2$–$C_4$ alkynyl, $R^2$ is phenyl optionally having substituents or heterocycle optionally having substituents, $X^1$, $X^2$, $X^3$ and $X^4$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio or the like, and $r_1$ and $r_2$ are each independently hydrogen, $C_1$–$C_4$ alkyl or the like, having excellent fungicidal activity and being useful as a fungicide for agricultural and horticultural use, and methods for preparation thereof.

5 Claims, No Drawings

BENZAMIDOXIME DERIVATIVES, PROCESS PRODUCTION THEREOF, AND AGROHORTICULTURAL BACTERICIDE

This application is a 371 of PCT/JP95/02596 filed Dec. 18, 1995.

TECHNICAL FIELD

The present invention relates to novel benzamidoxime derivatives, methods for preparation thereof and fungicides for agricultural and horticultural uses.

BACKGROUND ART

In farming of agricultural and horticultural crops in the past, various fungicides have been used for the control of plant diseases on the crops, however, many of them are not enough useful because of their insufficient effectiveness in plant disease control, the limitation in their use due to the appearance of resistant strain of plant disease pathogens to the fungicides, the development of phytotoxicity and contamination to the crops, and/or their strong toxicity to humans, domestic animals and wildlife. For this reason, there is still intensive requirement to develop safe fungicides for agricultural and horticultural uses, which do not have the disadvantages as described above.

Some benzamidoxime derivatives, which are close to the compounds of the present invention, and their use as fungicides have been disclosed in Japanese Patent Laid-opened No. Hei 2-6453 Gazette. However, it is obvious that the biological activity of those benzamide oxime derivatives are not enough in the practical plant disease control.

Therefore, it is an object of the present invention to provide novel compounds which can be a fungicide for agricultural and horticultural use capable of advantageously manufacturing the compound in an industrial scale, controlling plant diseases steadily and using it safely.

DISCLOSURE OF THE INVENTION

The present invention is directed to benzamidoxime derivatives represented by a general formula [I];

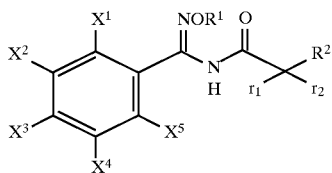

wherein $R^1$ is unsubstituted or substituted $C_1$–$C_4$ alkyl, unsubstituted or substituted $C_2$–$C_4$ alkenyl or unsubstituted or substituted $C_2$–$C_4$ alkynyl, $R^2$ is phenyl optionally having substituents or heterocycle optionally having substituents, $X^1$ is $C_1$–$C_4$ haloalkyl, $X^2$, $X^3$, $X^4$ and $X^5$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, and $r^1$ and $r^2$ are each independently hydrogen, halogen, $C_1$–$C_4$ alkyl, $C_1$–$C_4$ haloalkyl, $C_1$–$C_4$ alkoxy, $C_1$–$C_4$ alkylthio or amino, or $r^1$ and $r^2$ may form carbonyl in together, and, the present invention is also directed to methods for preparation thereof and fungicides for agricultural and horticultural use comprising the said derivatives.

In the present invention, for the examples of $C_1$–$C_4$ alkyl of the unsubstituted or substituted $C_1$–$C_4$ alkyl represented by $R^1$, methyl, ethyl, propyl, isopropyl, butyl, isobutyl and t-butyl can be given.

For the examples of $C_2$–$C_4$ alkenyl of the unsubstituted or substituted $C_2$–$C_4$ alkenyl represented by $R^1$, vinyl, 1-propenyl, 2-propenyl, isopropenyl, 1-butenyl, 2-butenyl and 3-butenyl can be given. For the examples of $C_2$–$C_4$ alkynyl of the unsubstituted or substituted $C_2$–$C_4$ alkynyl represented by $R^1$, ethynyl, propargyl, 2-butynyl and 3-butynyl can be given.

Further, in all of the unsubstituted or substituted $C_1$–$C_4$ alkyl, the unsubstituted or substituted $C_2$–$C_4$ alkenyl and the unsubstituted or substituted $C_2$–$C_4$ alkynyl represented by $R^1$; $C_3$–$C_8$ cycloalkyl, such as cyclopropyl, cyclobutyl, cyclopentyl, cyclohexyl and cycloheptyl; $C_3$–$C_8$ halocycloalkyl, such as 1-fluorocyclopropyl, 2-fluorocyclopropyl, 1-chlorocyclopropyl, 2-chlorocyclopropyl, 2,2-difluorocyclopropyl, 2,2-dichlorocyclopropyl, 2-fluorocyclopentyl, 3-fluorocyclopentyl, 2-chlorocyclopentyl, 3-chlorocyclopentyl, 3,4-difluorocyclohexyl, 3,4-dichlorocyclohexyl and 3,4-dibromosilocyclohexy 1; $C_3$–$C_8$ cycloalkenyl, such as 2-cyclohexenyl and 3-cyclohexenyl; halogens, such as fluorine, chlorine, bromine and iodine; $C_1$–$C_4$ alkoxy, such as methoxy, ethoxy, propyloxy, isopropyloxy, butyloxy, isobutyloxy and t-butyloxy; unsubstituted, mono-substituted or di-substituted amino by $C_1$–$C_4$ alkyl, such as amino, methylamino and dimethylamino; unsubstituted, mono-substituted or di-substituted carbamoyl by $C_1$–$C_4$ alkyl, such as carbamoyl, methylcarbamoyl and dimethylcarbamoyl; $C_1$–$C_4$ alkylthio, such as methylthio, ethylthio, propylthio and isopropylthio; $C_1$–$C_4$ alkylsulfinyl, such as methylsulfinyl and ethylsulfinyl; $C_1$–$C_4$ alkylsulfonyl, such as methylsulfonyl and ethylsulfonyl; $C_1$–$C_4$ alkoxycarbonyl, such as methoxycarbonyl and ethoxycarbonyl; carboxy and cyano, can be given for the examples of the substituents for any of $C_1$–$C_4$ alkyl, $C_2$–$C_4$ alkenyl and $C_2$–$C_4$ alkynyl.

However, straight chain or branched $C_1$–$C_4$ alkyl being unsubstituted or substituted is more preferable for the examples of the substituent represented by $R^1$. More particularly, straight chain or branched $C_1$–$C_4$ alkyl, such as methyl, ethyl, propyl, isopropyl, butyl, s-butyl and t-butyl; a group represented by a general formula, $R^3CH_2$, wherein $R^3$ is $C_3$–$C_8$ cycloalkyl, $C_1$–$C_3$ haloalkyl, $C_1$–$C_3$ alkoxy, $C_1$–$C_3$ alkylthio, $C_1$–$C_3$ alkylsulfinyl, $C_1$–$C_3$ alkylsulfonyl, $C_1$–$C_3$ alkoxycarbonyl, cyano, amino, $C_1$–$C_3$ monoalkylamino, $C_1$–$C_3$ dialkylamino or acylamino, such as $C_1$–$C_8$ cycloalkylmethyl including cyclopropylmethyl, cyclobutylmethyl, cyclopentylmethyl and cyclohexylmethyl, $C_1$–$C_8$ cyclohaloalkylmethyl including 2-fluorocyclopropylmethyl, 1-fluorocyclopropylmethyl, 1,2-difluorocyclopropylmethyl and 3,4-dibromocyclohexyl, $C_1$–$C_4$ haloalkyl including 2-chloroethyl, 2-fluoroethyl, 2,2-dichloroethyl, 2,2-difluoroethyl and 2,2,2-trifluoroethyl, $C_1$–$C_4$ alkoxymethyl including methoxymethyl, ethoxymethyl and propoxymethyl, $C_2$–$C_4$ alkynyl including propargyl, $C_2$–$C_4$ alkenyl including allyl, 2-butenyl, cyanomethyl, alkoxycarbonylmethyl including methoxycarbonylmethyl and ethoxycarbonylmethyl, alkylthiomethyl including methylthiomethyl and ethylthiomethyl, alkylsulfinylmethyl including methylsulfinylmethyl and ethylsulfinylmethyl, alkylsulfonylmethyl including methylsulfonylmethyl and ethylsulfonylmethyl, aminomethyl, substituted aminomethyl including N-methylaminomethyl, N,N-dimethylaminomethyl, N-acetylaminomethyl and N-benzoylaminomethyl, can be given for the examples of the straight chain or branched $C_1$–$C_4$ alkyl being unsubstituted or unsubstituted described above.

For the examples of heterocycle of the unsubstituted or substituted heterocycle group represented by $R^2$, 5- or 6-membered aromatic heterocycle containing 1–4 heteroatoms, such as N, O and S, such as pyridine ring, fran ring, thiophene ring, pyrazole ring, imidazole ring, triazole ring, pyrrole ring, pyrazine ring, pyrimidine ring, pyridazine ring, oxazole ring, isoxazole ring and thiazole ring, can be given.

The substituents for phenyl and heterocycle represented by $R^2$ may substitute one or more optional positions of the benzene ring or the heterocycle thereof and may be different with each other if 2 or more positions are substituted thereby. For the preferable examples of the substituents described hereinabove, halogens, such as fluorine, chlorine and bromine, $C_1$–$C_4$ alkyl, such as methyl, ethyl, propyl, isopropyl, butyl and t-butyl, $C_1$–$C_4$ alkoxy, such as methoxy, ethoxy, propoxy, isopropoxy, butoxy and t-butoxy, $C_2$–$C_4$ alkenyloxy, such as allyoxy and crotyloxy, $C_2$–$C_4$ alkynyloxy, such as propargyloxy, $C_1$–$C_4$ haloalkyl, such as chloromethyl, fluoromethyl, bromomethyl, dichloromethyl, difluoromethyl, trichloromethyl, trifluoromethyl, tribromomethyl, trifluoroethoxy and pentafluoroethoxy, and $C_1$–$C_4$ haloalkoxy, such as chloromethoxy, fluoromethoxy, bromomethoxy, dichloromethoxy, difluoromethoxy, trichloromethoxy, trifluoromethoxy, tribromomethoxy and trifluoroethoxy, can be given, For the examples of the $C_1$–$C_4$ haloalkyl represented by $X^1$, straight chain or branched $C_1$–$C_4$ haloalkyl, such as chloromethyl, dichloromethyl, trichloromethyl, difluoromethyl, trifluoromethyl, bromomethyl, dibromomethyl, chloroethyl, fluoroethyl, dichloroethyl, difluoroethyl, trifluoroethyl, tetrafluoroethyl, pentafluoroethyl, chloropropyl, fluoropropyl, perfluoropropyl, chloroisopropyl, fluoroisopropyl, perfluoroisopropyl, chlorobutyl, fluorobutyl, perfluorobutyl, chloroisobutyl, fluoroisobutyl, perfluoroisobutyl, chloro-s-butyl, fluoro-s-butyl, perfluoro-s-butyl, chloro-t-butyl, fluoro-t-butyl and perfluoro-t-butyl, can be given.

For the examples of halogen atoms represented by $X^2$, $X^3$, $X^4$ and $X^5$, fluorine, chlorine, bromine and iodine can be given, and for the examples of the $C_1$–$C_4$ alkyl represented by $X^2$, $X^3$, $X^4$ and $X^5$, methyl, ethyl, propyl, isopropyl, butyl, isobutyl and t-butyl can be given, and further for the examples of the $C_1$–$C_4$ haloalkyl represented by $X^2$, $X^3$, $X^4$ and $X^5$, straight chain or branched $C_1$–$C_4$ haloalkyl, such as chloromethyl, dichloromethyl, trichloromethyl, difluoromethyl, trifluoromethyl, bromomethyl, dibromomethyl, chloroethyl, fluoroethyl, dichloroethyl, difluoroethyl, trifluoroethyl, tetrafluoroethyl, pentafluoroethyl, chloropropyl, fluoropropyl, perfluoropropyl, chloroisopropyl, fluoroisopropyl, perfluoroisopropyl, chlorobutyl, fluorobutyl, perfluorobutyl, chloroisobutyl, fluoroisobutyl, perfluoroisobutyl, chloro-s-butyl, fluoro-s-butyl, perfluoro-s-butyl, chloro-t-butyl, fluoro-t-butyl and perfluoro-t-butyl, can be given, and still for the examples of the $C_1$–$C_4$ alkoxy represented by $X^2$, $X^3$, $X^4$ and $X^5$, methoxy, ethoxy, propyloxy, isopropyloxy, butyloxy, isobutyloxy and t-butyloxy can be given. In addition, for the examples of the $C_1$–$C_4$ alkylthio represented by $X^2$, $X^3$, $X^4$ and $X^5$, methylthio, ethylthio, propylthio, isopropylthio, butylthio, isobutylthio and t-butylthio can be given, and for the examples of the $C_1$–$C_4$ haloalkoxy represented by $X^2$, $X^3$, $X^4$ and $X^5$, trifluoromethoxy, difluoromethoxy, trichloromethoxy, trifluoroethoxy and tetrafluoroethoxy can be given.

Furthermore, for the examples of the groups represented by $r^1$ and $r^2$, which may be the same or different groups with each other, hydrogen, halogen atoms, such as fluorine, chlorine, bromine and iodine, $C_1$–$C_4$ alkyl, such as methyl, ethyl, propyl, isopropyl, butyl and t-butyl, $C_1$–$C_4$ alkoxy, such as methoxy, ethoxy, propoxy, isopropoxy, butoxy and t-butoxy, $C_1$–$C_4$ alkylthio, such as methylthio, ethylthio, propylthio, ispropylthio, butylthio and t-butylthio, $C_1$–$C_4$ haloalkyl, such as trifluoromethyl, trichloromethyl, tribromomethyl, trifluoroethyl, chloromethyl, fluoromethyl and pentafluoroethyl, and amino can be given. Moreover, $r^1$ and $r^2$ may in together form a carbonyl group.

(Manufacturing of the Compounds)

The compounds of the present invention can be manufactured according to the following reaction formula;

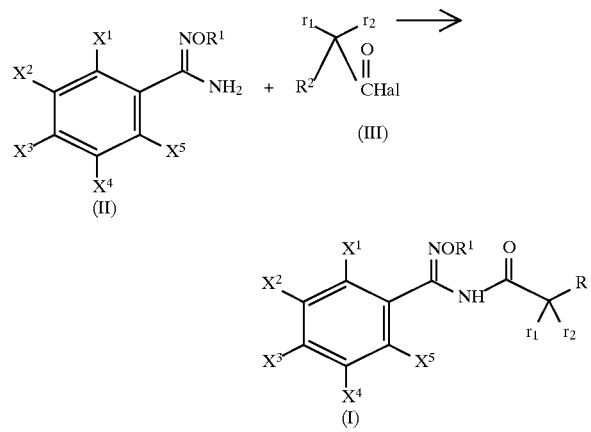

wherein Hal represents halogen, and $R^1$, $R^2$, $X^1$, $X^2$, $X^3$, $X^4$, $X^5$, $r_1$ and $r_2$ are as described above.

The reaction described above is carried out by reacting the compound represented by the general formula [II] and the compound represented by the general formula [III] in an organic solvent for from 10 min. to several dozens of hours at a temperature range of from 0° C. to the boiling point of the solvent used and in the presence of a base, if appropriate.

For the examples of the solvent usable in the reaction described above, aromatic hydrocarbons, such as benzene and toluene, ethers, such as THF and diethyl ether, halogenated hydrocarbons, such as chloroform and dichloro methane, amides, such as DMF, DMSO, acetonitrile and the mixture of the solvent exemplified above, can be given.

As the base usable in the reaction, pyridine, triethyl amine, DBU, sodium hydroxide, sodium carbonate, potassium carbonate or the like can be exemplified.

After completed the reaction, the objective compounds can be obtained by taking an ordinary post-treatment procedure and allowing the products to the purification by using silica gel column chromatography or the else.

Whereas, the raw material compound of the present invention, represented by the general formula [II] can be synthesized according to the following reaction formula;

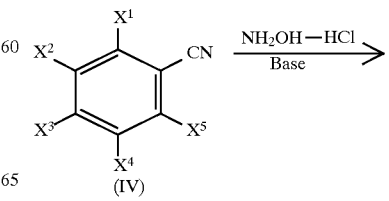

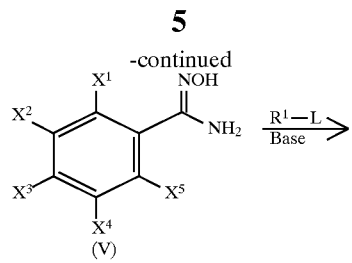

wherein L is an eliminating group, such as paratoluenesulfonyloxy, methylsulfonyloxy and halogen atoms, and $R^1$, $X^1$, $X^2$, $X^3$, $X^4$ and $X^5$ are as described above.

The first step reaction in the reaction formula shown above is to obtain a benzamide oxime compound represented by the general formula [V], wherein a nitrile compound represented by the general formula [IV] and hydroxyl amine hydrochloride are allowed to a reaction for 10 min. to several dozens of hours in an inactive solvent and in the presence of a base at a temperature range of from 0° C. to the boiling point of the solvent used.

For the examples of the solvent usable in the reaction described above, alcohols, such as methanol, ethanol and propanol, ethers, such as THF and diethyl ether, amides, such as DMF, DMSO, water and the mixture of the solvent exemplified hereinabove, can be given.

Further, for the examples of the base usable in the reaction described above, sodium carbonate, sodium hydrogencarbonate, potassium carbonate, sodium hydroxide, potassium hydroxide, triethyl amine, pyridine and the like can be given.

The second step reaction in the reaction formula shown above is to obtain the raw material compound represented by the general formula [II], wherein the compound represented by the general formula [V] and a compound represented by a general formula, $R^1$—L, are allowed to a reaction for 10 min. to several dozens of hours in a solvent and in the presence of a base at a temperature range of from −15° C. to the boiling point of the solvent used.

For the examples of the base usable in the second step reaction, metal alkoxide, such as sodium methoxide and sodium ethoxide, inorganic bases, such as sodium hydride, sodium hydroxide, potassium hydroxide and potassium carbonate, and organic bases, such as triethyl amine and pyridine, can be given.

Furthermore, if appropriate, catalysts may be used in the second step reaction, though it depends on the type of the solvent and the base to be used. For the examples of the catalysts usable in the reaction, crown ethers, such as 18-crown-6 and dicyclohexyl-18-crown-6, tetrabutyl ammonium bromide and other chlorides, quaternary ammonium salts, such as methyltrioctyl ammonium chloride and benzyltriethyl ammonium chloride, and phosphonium salts, such as tetraphenyl phosphonium bromide and hexadecyltributyl phosphonium iodide, can be given.

The chemical structures of the compounds of the present invention were determined by using NMR, IR, MS and the other analytical apparatuses.

BEST MODE FOR CARRYING OUT THE INVENTION

Now, the present invention is further described in detail with referring to the examples described hereinbelow.

EXAMPLE 1
Preparation of N'-cyclopropylmethyloxy-N-(4-methoxyphenyl)acetyl-2-fluoro-6-trifluoromethylbenzamidine(Compound No. 56)

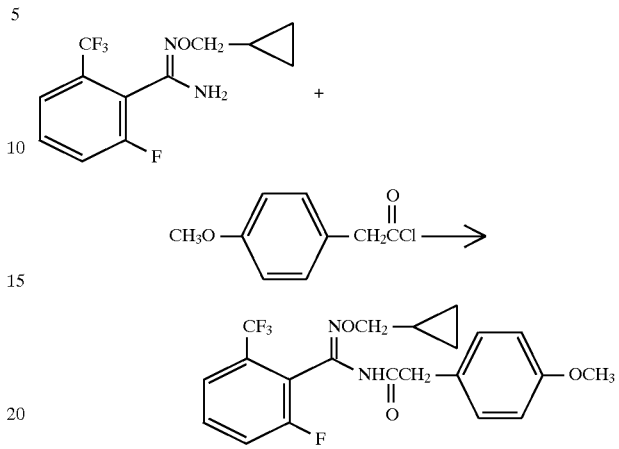

In 200 ml of benzene was dissolved 20.0 g of N'-cyclopropylmethyloxy-2-fluoro-6-trifluoromethylbenzamidine, and to the solution was added 16.0 g of 4-methoxyphenylacetylchloride. The solution was heated under refluxing for 10 hours. After cooling, ethyl acetate was added to the solution, followed by washing with water and drying over anhydrous magnesium sulfate. The organic layer was concentrated under reduced pressure and the residue was subjected to silica gel column chromatography to obtain 23.6 g of the objective compound.m.p. 75°–76° C.

EXAMPLE 2
Preparation N'-cyclopropylmethyloxy-N-(4-methoxyphenyl)acetyl-2-trifluoromethyl benzamidine (Compound No. 12)

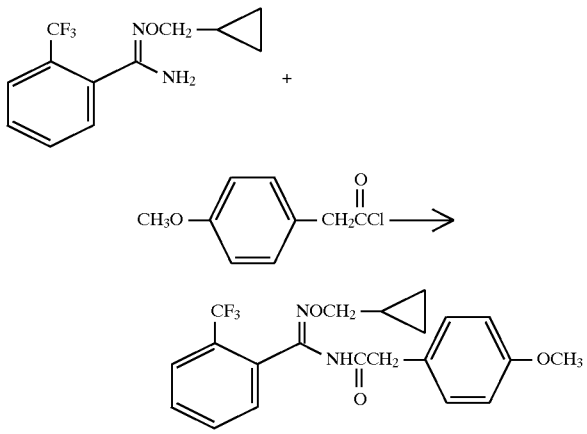

In 80 ml of benzene was dissolved 10.4 g of N'-cyclopropylmethyloxy-2-fluoro-6-trifluoromethylbenzamidine, and to the solution was added 8.9 g of 4-methoxyphenylacetylchloride. The solution was heated under refluxing for 3 hours. After cooling, ethyl acetate was added to the solution, followed by washing with water and drying over anhydrous magnesium sulfate. The organic layer was concentrated under reduced pressure and the residue obtained in crystal was washed with a mixed solvent hexane and ether to thereby obtain 13.7 g of crude crystal. The crystal was then re-crystallized in hexane, thereby affording 11.5 g of the objective compound.m.p. 88°–90° C.

Now, the examples for preparing the raw material compounds described above to be used for the preparing of the compounds of the present invention are described hereinbelow.

Reference Example 1
Preparation of 2-fluoro-6-trifluoromethylbenzamidoxime

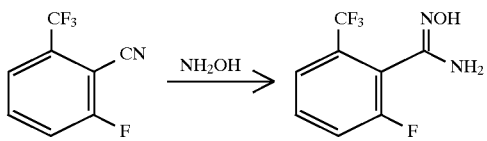

In 540 ml of methanol was dissolved 58.8 g of hydroxylamine hydrochloride and to the solution was added 160 ml of aqueous solution of sodium carbonate containing 49.4 g thereof. 40 g of 2-fluoro-6-trifluoromethylbenzonitrile was added thereto at room temperature with stirring, and then further stirred 3 hours at 60° C. After removing the solvent methanol by distillation from the solution, the solution was extracted with ethyl acetate. The organic layer was dried over anhydrous magnesium sulfate, and it was concentrated under reduced pressure, thereby obtaining crude crystals. The crystals were then added with 200 ml of 3N aqueous solution of hydrochloric acid and thoroughly stirred, then the insoluble substance resulted in the solution was removed by filtration. The filtrate was then neutralized with 10% aqueous solution of sodium hydroxide under cooling and then extracted again with ethyl acetate. The organic layer was dried over anhydrous magnesium sulfate, and the solution was concentrated under reduced pressure to obtain 26.6 g of the objective compound.

m.p. 155°–157° C.

The examples of benzamide oxime derivatives represented by the general formula [V], which can be manufactured according to the methods as described above, are given in Table 1 hereinbelow.

TABLE 1

Chemical formula

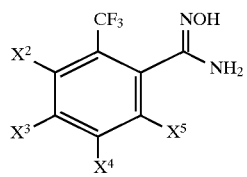

| $X^2$ | $X^3$ | $X^4$ | $X^5$ | Physical const. |
|---|---|---|---|---|
| H | H | H | H | mp 124–126° C. |
| H | H | H | Cl | mp 112–115° C. |
| H | H | Cl | F | mp 107–108° C. |
| H | H | Cl | Cl | $n_D^{24.0}$ 1.5210 |
| H | H | H | F | mp 155–157° C. |
| H | H | F | F | mp 105–107° C. |
| H | H | F | Cl | mp 98–99° C. |
| H | H | $CF_3$ | Cl | mp 97–99° C. |

Reference Example 2
Preparation of N'-cyclopropylmethyloxy-2-fluoro-6-trifluoromethylbenzamidine

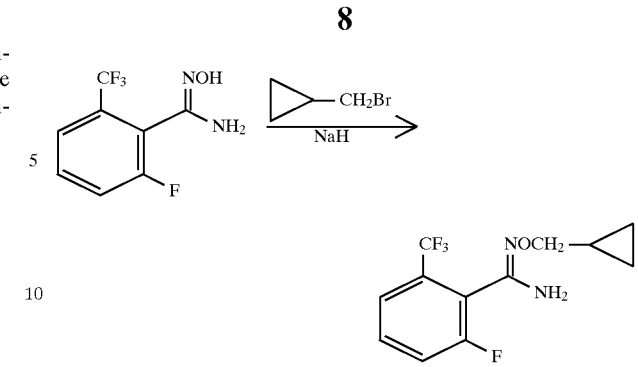

In 100 ml of DMF was dissolved 26.6 g of 2-fluoro-6-trifluoromethylbenzamidoxime and 17.8 g of cyclopropylmethylbromide, and to the solution was added 4.8 g of sodium hydride (60% in oil) at 10° C. over 30 min. The solution was then stirred for 3 hours, and the solution reacted was poured into ice-water and extracted with ethyl acetate. The organic layer was washed with water and dried over anhydrous magnesium sulfate. The organic layer was concentrated under reduced pressure and the residue was subjected to silica gel column chromatography to obtain 24.8 g of the objective compound.

m.p. 63°–64° C.

Reference Examples 3
Preparation of N'-cyclopropylmethyloxy-3,6-bistrifluoromethyl-2-chlorobenzamidine
Preparation of N'-cyclopropylmethyloxy-3,6-bistrifluoromethyl-2-chlorobenzamidine

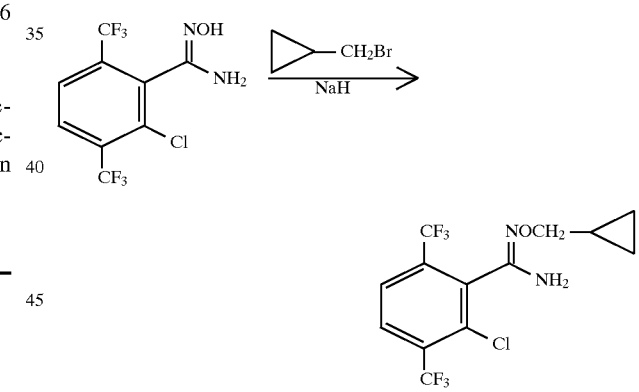

In 10 ml of chloroform was dissolved 0.60 g of 3,6-bistrifluoromethyl-2-chlorobenzamidoxime and 0.50 g of cyclopropylmethylbromide, and to the solution was added 0.1 g of tetrabutylammonium bromide at room temperature with stirring, and then 1.2 ml of 10% aqueous solution of sodiunhydroxide, then stirred for 3 hours at 30°–40° C. The solution was washed with water, washed with saturated saline solution and dried over anhydrous magnesium sulfate. The organic layer was concentrated under reduced pressure and the residue was subjected to silica gel column chromatography to obtain 0.40 g of the objective compound.m.p. 75°–80° C.

The examples of benzamidoxime derivatives represented by the general formula [II], which can be prepared according to the methods similar to the methods as described above, are given in Table 2 hereinbelow.

TABLE 2

Chemical formula

[Structure: benzene ring with CF$_3$, C(=NOR$^1$)NH$_2$, and X$^2$, X$^3$, X$^4$, X$^5$ substituents]

| X$^2$ | X$^3$ | X$^4$ | X$^5$ | R$^1$ | Physical const. |
|---|---|---|---|---|---|
| H | H | H | H | CH$_2$cPr | $n_D^{24.5}$ 1.4917 |
| H | H | H | F | Et | mp 64–66° C. |
| H | H | H | F | iPr | $n_D^{24.0}$ 1.4789 |
| H | H | H | F | CH$_2$C(CH$_3$)$_3$ | mp 97–98° C. |
| H | H | H | F | CH$_2$CH=CH$_2$ | mp 69–70° C. |
| H | H | H | F | CH$_2$C≡CH | $n_D^{23.5}$ 1.5011 |
| H | H | H | Cl | CH$_2$cPr | mp 43–46° C. |
| H | H | Cl | F | CH$_2$cPr | mp 71–73° C. |
| H | H | Cl | Cl | CH$_2$C≡CH | $n_D^{23.5}$ 1.5360 |
| Cl | H | H | Cl | CH$_2$cPr | $n_D^{23.5}$ 1.5308 |
| H | H | Cl | Cl | CH$_2$cPr | mp 73–75° C. |
| H | H | F | F | CH$_2$cPr | mp 43–45° C. |
| H | H | F | Cl | CH$_2$cPr | mp 54–55° C. |
| H | H | CF$_3$ | Cl | CH$_2$cPr | mp 75–78° C. |

TABLE 2-continued

Chemical formula

[Structure: benzene ring with CF$_3$, C(=NOR$^1$)NH$_2$, and X$^2$, X$^3$, X$^4$, X$^5$ substituents]

| X$^2$ | X$^3$ | X$^4$ | X$^5$ | R$^1$ | Physical const. |
|---|---|---|---|---|---|

*cPr represnts cyclopropylmethyl in the tables.

Now, the representative examples for the compounds of the present invention, which can be manufactured according to the praparation methods similar to the ones described in Examples 1 and 2, are given in Tables 3 and 4. However, it should be noted that X$^1$, X$^2$, X$^3$, X$^4$, X$^5$, R$^1$, R$^2$, r$_1$ and r$_2$ given in the Tables 3 and 4 correspond to X$^1$, X$^2$, X$^3$, X$^4$, X$^5$, R$^1$, R$^2$, r$_1$ and r$_2$ given for the compounds represented by the general formula [I], respectively.

TABLE 3

(r$^1$, r$^2$ = H)

| No. | X$^1$ | X$^2$ | X$^3$ | X$^4$ | X$^5$ | R$^1$ | R$^2$ | Physical const. mp. (°C.) refractive index |
|---|---|---|---|---|---|---|---|---|
| 1 | CF$_3$ | H | H | H | H | Et | Ph-4-OMe | 72–73 |
| 2 | CF$_3$ | H | H | H | H | Me | Ph-4-OMe | |
| 3 | CF$_3$ | H | H | H | H | CH$_2$cPr | 2-thienyl | 93–95 |
| 4 | CF$_3$ | H | H | H | H | CH$_2$cPr | 3-thienyl | 92–93 |
| 5 | CF$_3$ | H | H | H | H | CH$_2$cPr | Ph-2,4-F$_2$ | 100–101 |
| 6 | CF$_3$ | H | H | H | H | CH$_2$cPr | Ph-2-F | 84–85 |
| 7 | CF$_3$ | H | H | H | H | CH$_2$cPr | Ph-2-F,4-OMe | 84–85 |
| 8 | CF$_3$ | H | H | H | H | CH$_2$cPr | Ph-3-Me | 81–82 |
| 9 | CF$_3$ | H | H | H | H | CH$_2$cPr | Ph-3-Me-4-OMe | 77–79 |
| 10 | CF$_3$ | H | H | H | H | CH$_2$cPr | Ph-4-F | 113–114 |
| 11 | CF$_3$ | H | H | H | H | CH$_2$cPr | Ph-4-Me | 80–81 |
| 12 | CF$_3$ | H | H | H | H | CH$_2$cPr | Ph-4-OMe | 88–90 |
| 13 | CF$_3$ | H | H | H | H | CH$_2$cPr | Ph | 100–102 |
| 14 | CF$_3$ | H | H | H | H | nBu | Ph-4-OMe | |
| 15 | CF$_3$ | H | H | H | H | tBu | Ph-4-OMe | |
| 16 | CF$_3$ | H | H | H | F | CH$_2$CH=CH$_2$ | Ph-4-OMe | $n_D^{27.0}$ 1.5290 |
| 17 | CF$_3$ | H | H | H | F | CH$_2$CH=CH$_2$ | Ph | $n_D^{26.5}$ 1.5132 |
| 18 | CF$_3$ | H | H | H | F | CH(CH$_3$)CH=CH$_2$ | Ph-4-OMe | 76–78 |
| 19 | CF$_3$ | H | H | H | F | CH$_2$CH=CHCl | Ph-4-OMe | $n_D^{25.4}$ 1.5333 |
| 20 | CF$_3$ | H | H | H | F | CH$_2$CH=CCl$_2$ | Ph-4-OMe | $n_D^{25.7}$ 1.5362 |
| 21 | CF$_3$ | H | H | H | F | CH$_2$CH=CH—CH$_3$ | Ph-4-OMe | $n_D^{23.2}$ 1.5148 |
| 22 | CF$_3$ | H | H | H | F | Et | Ph-4-OMe | 70–73 |
| 23 | CF$_3$ | H | H | H | F | Et | Ph | 59–61 |
| 24 | CF$_3$ | H | H | H | F | CH$_2$CH$_2$Cl | Ph-4-OMe | $n_D^{24.0}$ 1.5330 |
| 25 | CF$_3$ | H | H | H | F | CH$_2$CHF$_2$ | Ph-4-OMe | 78–80 |
| 26 | CF$_3$ | H | H | H | F | Me | Ph-4-OMe | |
| 27 | CF$_3$ | H | H | H | F | CH$_2$C(Cl)=CH$_2$ | Ph-4-OMe | $n_D^{25.5}$ 1.5242 |
| 28 | CF$_3$ | H | H | H | F | CH$_2$C(CH$_3$)=CH$_2$ | Ph-4-OMe | $n_D^{25.0}$ 1.5162 |
| 29 | CF$_3$ | H | H | H | F | CH$_2$CN | Ph-4-OMe | $n_D^{23.5}$ 1.5113 |
| 30 | CF$_3$ | H | H | H | F | CH$_2$CN | Ph | $n_D^{23.5}$ 1.5226 |
| 31 | CF$_3$ | H | H | H | F | CH$_2$OCH$_3$ | Ph-4-OMe | $n_D^{24.0}$ 1.5288 |
| 32 | CF$_3$ | H | H | H | F | CH$_2$OCH$_3$ | Ph | $n_D^{24.5}$ 1.5279 |
| 33 | CF$_3$ | H | H | H | F | CH$_2$cPr | 3-methyl-pyrazol-1-yl | $n_D^{21.8}$ 1.5133 |
| 34 | CF$_3$ | H | H | H | F | CH$_2$cPr | 4-methyl-pyrazol-1-yl | $n_D^{23.6}$ 1.5121 |

TABLE 3-continued ($r^1, r^2 = H$)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 35 | $CF_3$ | H | H | H | F | $CH_2cPr$ | pyrazol-1-yl | $n_D^{22.9}$ 1.5126 |
| 36 | $CF_3$ | H | H | H | F | $CH_2cPr$ | 3-methyl-2-thienyl | $n_D^{23.2}$ 1.5310 |
| 37 | $CF_3$ | H | H | H | F | $CH_2cPr$ | 4-methyl-2-thienyl | $n_D^{23.2}$ 1.5313 |
| 38 | $CF_3$ | H | H | H | F | $CH_2cPr$ | 5-methyl-2-thienyl | $n_D^{23.9}$ 1.5353 |
| 39 | $CF_3$ | H | H | H | F | $CH_2cPr$ | 2-thienyl | $n_D^{22.2}$ 1.5346 |
| 40 | $CF_3$ | H | H | H | F | $CH_2cPr$ | 4-methyl-3-thienyl | $n_D^{26.5}$ 1.5302 |
| 41 | $CF_3$ | H | H | H | F | $CH_2cPr$ | 5-methyl-3-thienyl | 57–58 |
| 42 | $CF_3$ | H | H | H | F | $CH_2cPr$ | 3-thienyl | 70–72 |
| 43 | $CF_3$ | H | H | H | F | $CH_2cPr$ | Ph-2,4-$F_2$ | $n_D^{26.0}$ 1.5083 |
| 44 | $CF_3$ | H | H | H | F | $CH_2cPr$ | Ph-2-F | $n_D^{26.0}$ 1.5191 |
| 45 | $CF_3$ | H | H | H | F | $CH_2cPr$ | Ph-2-F-3-Me | $n_D^{23.4}$ 1.5197 |
| 46 | $CF_3$ | H | H | H | F | $CH_2cPr$ | Ph-2-F-4-OMe | $n_D^{27.5}$ 1.5193 |
| 47 | $CF_3$ | H | H | H | F | $CH_2cPr$ | Ph-2-F-4-OMe-5-Me | $n_D^{27.0}$ 1.6190 |
| 48 | $CF_3$ | H | H | H | F | $CH_2cPr$ | Ph-2-F-5-Me | $n_D^{26.7}$ 1.5143 |
| 49 | $CF_3$ | H | H | H | F | $CH_2cPr$ | Ph-3,5-$Me_2$ | 88–89 |
| 50 | $CF_3$ | H | H | H | F | $CH_2cPr$ | Ph-3-Et | 63–64 |
| 51 | $CF_3$ | H | H | H | F | $CH_2cPr$ | Ph-3-Me | 52–53 |
| 52 | $CF_3$ | H | H | H | F | $CH_2cPr$ | Ph-3-Me-4-F | 73–74 |
| 53 | $CF_3$ | H | H | H | F | $CH_2cPr$ | Ph-3-Me-4-OMe | $n_D^{26.0}$ 1.5307 |
| 54 | $CF_3$ | H | H | H | F | $CH_2cPr$ | Ph-4-F | 58–59 |
| 55 | $CF_3$ | H | H | H | F | $CH_2cPr$ | Ph-4-Me | $n_D^{26.0}$ 1.5248 |
| 56 | $CF_3$ | H | H | H | F | $CH_2cPr$ | Ph-4-OMe | 75–76 |
| 57 | $CF_3$ | H | H | H | F | $CH_2cPr$ | Ph | 72–74 |
| 58 | $CF_3$ | H | H | H | F | $CH_2C{\equiv}CH$ | 2-thienyl | 54–56 |
| 59 | $CF_3$ | H | H | H | F | $CH_2C{\equiv}CH$ | 3-thienyl | 56–58 |
| 60 | $CF_3$ | H | H | H | F | $CH_2C{\equiv}CH$ | Ph-2-F | 57–58 |
| 61 | $CF_3$ | H | H | H | F | $CH_2C{\equiv}CH$ | Ph-2-F-4-OMe | $n_D^{22.5}$ 1.5257 |
| 62 | $CF_3$ | H | H | H | F | $CH_2C{\equiv}CH$ | Ph-2-F-5-Me | $n_D^{26.0}$ 1.5192 |
| 63 | $CF_3$ | H | H | H | F | $CH_2C{\equiv}CH$ | Ph-3,5-$Me_2$ | 98–100 |
| 64 | $CF_3$ | H | H | H | F | $CH_2C{\equiv}CH$ | Ph-4-Me | 95–96 |
| 65 | $CF_3$ | H | H | H | F | $CH_2C{\equiv}CH$ | Ph-4-OMe | $n_D^{27.5}$ 1.5370 |
| 66 | $CF_3$ | H | H | H | F | $CH_2C{\equiv}CH$ | Ph | 58–60 |
| 67 | $CF_3$ | H | H | H | F | $CH_2C{\equiv}Cl$ | Ph-4-OMe | $n_D^{22.5}$ 1.5557 |
| 68 | $CF_3$ | H | H | H | F | iPr | Ph-4-OMe | 85–86 |
| 69 | $CF_3$ | H | H | H | F | iPr | Ph | 84–85 |
| 70 | $CF_3$ | H | H | H | F | nBu | Ph | |
| 71 | $CF_3$ | H | H | H | F | nPr | Ph-2-F-4-OMe | $n_D^{18.5}$ 1.5121 |
| 72 | $CF_3$ | H | H | H | F | nPr | Ph-2-F-5-Me | $n_D^{18.0}$ 1.5129 |
| 73 | $CF_3$ | H | H | H | F | nPr | Ph-4-Me | 59–60 |
| 74 | $CF_3$ | H | H | H | F | nPr | Ph-4-OMe | 54–55 |
| 75 | $CF_3$ | H | H | H | F | nPr | Ph | $n_D^{26.5}$ 1.5106 |
| 76 | $CF_3$ | H | H | H | F | tBu | Ph | |
| 77 | $CF_3$ | H | H | H | Cl | $CH_2CH{=}CH_2$ | Ph-4-OMe | |
| 78 | $CF_3$ | H | H | H | Cl | $CH(CH_3)CH{=}CH_2$ | Ph-4-OMe | |
| 79 | $CF_3$ | H | H | H | Cl | $CH_2CH{=}CHCl$ | Ph-4-OMe | |
| 80 | $CF_3$ | H | H | H | Cl | $CH_2CH{=}CCl_2$ | Ph-4-OMe | |
| 81 | $CF_3$ | H | H | H | Cl | $CH_2CH{=}CHCH_3$ | Ph-4-OMe | |
| 82 | $CF_3$ | H | H | H | Cl | Et | Ph-4-OMe | 68–70 |
| 83 | $CF_3$ | H | H | H | Cl | $CH_2CH_2Cl$ | Ph-4-OMe | |
| 84 | $CF_3$ | H | H | H | Cl | $CH_2CHF_2$ | Ph-4-OMe | |
| 85 | $CF_3$ | H | H | H | Cl | Me | Ph-4-OMe | |
| 86 | $CF_3$ | H | H | H | Cl | $CH_2C(Cl){=}CH_2$ | Ph-4-OMe | |
| 87 | $CF_3$ | H | H | H | Cl | $CH_2C(CH_3){=}CH_2$ | Ph-4-OMe | |
| 88 | $CF_3$ | H | H | H | Cl | $CH_2CN$ | Ph-4-OMe | |
| 89 | $CF_3$ | H | H | H | Cl | $CH_2OMe$ | Ph-4-OMe | |
| 90 | $CF_3$ | H | H | H | Cl | $CH_2cPr$ | 3-methyl-pyrazol-1-yl | |
| 91 | $CF_3$ | H | H | H | Cl | $CH_2cPr$ | 4-methyl- | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 92 | $CF_3$ | H | H | H | Cl | $CH_2cPr$ | pyrazol-1-yl | |
| 93 | $CF_3$ | H | H | H | Cl | $CH_2cPr$ | 3-methyl-2-thienyl | |
| 94 | $CF_3$ | H | H | H | Cl | $CH_2cPr$ | 4-methyl-2-thienyl | |
| 95 | $CF_3$ | H | H | H | Cl | $CH_2cPr$ | 5-methyl-2-thienyl | |
| 96 | $CF_3$ | H | H | H | Cl | $CH_2cPr$ | 2-thienyl | 47–49 |
| 97 | $CF_3$ | H | H | H | Cl | $CH_2cPr$ | 4-methyl-3-thienyl | |
| 98 | $CF_3$ | H | H | H | Cl | $CH_2cPr$ | 5-methyl-3-thienyl | |
| 99 | $CF_3$ | H | H | H | Cl | $CH_2cPr$ | 3-thienyl | 74–76 |
| 100 | $CF_3$ | H | H | H | Cl | $CH_2cPr$ | Ph-2,4-$F_2$ | |
| 101 | $CF_3$ | H | H | H | Cl | $CH_2cPr$ | Ph-2-F | |
| 102 | $CF_3$ | H | H | H | Cl | $CH_2cPr$ | Ph-2-F-3-Me | |
| 103 | $CF_3$ | H | H | H | Cl | $CH_2cPr$ | Ph-2-F-4-OMe | |
| 104 | $CF_3$ | H | H | H | Cl | $CH_2cPr$ | Ph-2-F-4-OMe-5-Me | |
| 105 | $CF_3$ | H | H | H | Cl | $CH_2cPr$ | Ph-2-F-5-Me | $n_D^{23.8}$ 1.5323 |
| 106 | $CF_3$ | H | H | H | Cl | $CH_2cPr$ | Ph-3,5-$Me_2$ | |
| 107 | $CF_3$ | H | H | H | Cl | $CH_2cPr$ | Ph-3-Me | |
| 108 | $CF_3$ | H | H | H | Cl | $CH_2cPr$ | Ph-3-Me-4-F | |
| 109 | $CF_3$ | H | H | H | Cl | $CH_2cPr$ | Ph-3-Me-4-OMe | |
| 110 | $CF_3$ | H | H | H | Cl | $CH_2cPr$ | Ph-4-F | |
| 111 | $CF_3$ | H | H | H | Cl | $CH_2cPr$ | Ph-4-Me | |
| 112 | $CF_3$ | H | H | H | Cl | $CH_2cPr$ | Ph-4-OMe | 65–67 |
| 113 | $CF_3$ | H | H | H | Cl | $CH_2cPr$ | Ph | 63–65 |
| 114 | $CF_3$ | H | H | H | Cl | $CH_2C\equiv CH$ | Ph-4-OMe | 76–78 |
| 115 | $CF_3$ | H | H | H | Cl | $CH_2C\equiv CH$ | Ph | 96–97 |
| 116 | $CF_3$ | H | H | H | Cl | $CH_2C\equiv Cl$ | Ph-4-OMe | |
| 117 | $CF_3$ | H | H | H | Cl | iPr | Ph-4-OMe | |
| 118 | $CF_3$ | H | H | H | Cl | nBu | Ph-4-OMe | |
| 119 | $CF_3$ | H | H | H | Cl | nPr | Ph-4-OMe | |
| 120 | $CF_3$ | H | H | H | Cl | tBu | Ph-4-OMe | |
| 121 | $CF_3$ | H | H | H | $CF_3$ | $CH_2CH=CH_2$ | Ph-4-OMe | |
| 122 | $CF_3$ | H | H | H | $CF_3$ | $CH(CH_3)CH=CH_2$ | Ph-4-OMe | |
| 123 | $CF_3$ | H | H | H | $CF_3$ | $CH_2CH=CHCl$ | Ph-4-OMe | |
| 124 | $CF_3$ | H | H | H | $CF_3$ | $CH_2CH=CCl_2$ | Ph-4-OMe | |
| 125 | $CF_3$ | H | H | H | $CF_3$ | $CH_2CH=CHCH_3$ | Ph-4-OMe | |
| 126 | $CF_3$ | H | H | H | $CF_3$ | Et | Ph-4-OMe | |
| 127 | $CF_3$ | H | H | H | $CF_3$ | $CH_2CH_2Cl$ | Ph-4-OMe | |
| 128 | $CF_3$ | H | H | H | $CF_3$ | $CH_2CHF_2$ | Ph-4-OMe | |
| 129 | $CF_3$ | H | H | H | $CF_3$ | Me | Ph-4-OMe | |
| 130 | $CF_3$ | H | H | H | $CF_3$ | $CH_2C(Cl)=CH_2$ | Ph-4-OMe | |
| 131 | $CF_3$ | H | H | H | $CF_3$ | $CH_2C(CH_3)=CH_2$ | Ph-4-OMe | |
| 132 | $CF_3$ | H | H | H | $CF_3$ | $CH_2CN$ | Ph-4-OMe | |
| 133 | $CF_3$ | H | H | H | $CF_3$ | $CH_2OMe$ | Ph-4-OMe | |
| 134 | $CF_3$ | H | H | H | $CF_3$ | $CH_2cPr$ | 3-methyl-pyrazol-1-yl | |
| 135 | $CF_3$ | H | H | H | $CF_3$ | $CH_2cPr$ | 4-methyl-pyrazol-1-yl | |
| 136 | $CF_3$ | H | H | H | $CF_3$ | $CH_2cPr$ | Ph pyrazol-1-yl | |
| 137 | $CF_3$ | H | H | H | $CF_3$ | $CH_2cPr$ | 3-methyl-2-thienyl | |
| 138 | $CF_3$ | H | H | H | $CF_3$ | $CH_2cPr$ | 4-methyl-2-thienyl | |
| 139 | $CF_3$ | H | H | H | $CF_3$ | $CH_2cPr$ | 5-methyl-2-thienyl | |
| 140 | $CF_3$ | H | H | H | $CF_3$ | $CH_2cPr$ | 2-thienyl | $n_D^{22.4}$ 1.5082 |
| 141 | $CF_3$ | H | H | H | $CF_3$ | $CH_2cPr$ | 4-methyl-3-thienyl | |
| 142 | $CF_3$ | H | H | H | $CF_3$ | $CH_2cPr$ | 5-methyl-3-thienyl | |
| 143 | $CF_3$ | H | H | H | $CF_3$ | $CH_2cPr$ | 3-thienyl | |
| 144 | $CF_3$ | H | H | H | $CF_3$ | $CH_2cPr$ | Ph-2,4-$F_2$ | |
| 145 | $CF_3$ | H | H | H | $CF_3$ | $CH_2cPr$ | Ph-2-F | |
| 146 | $CF_3$ | H | H | H | $CF_3$ | $CH_2cPr$ | Ph-2-F-3-Me | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 147 | $CF_3$ | H | H | H | $CF_3$ | $CH_2cPr$ | Ph-2-F-4-OMe | |
| 148 | $CF_3$ | H | H | H | $CF_3$ | $CH_2cPr$ | Ph-2-F-4-OMe-5-Me | |
| 149 | $CF_3$ | H | H | H | $CF_3$ | $CH_2cPr$ | Ph-2-F-5-Me | 74–75 |
| 150 | $CF_3$ | H | H | H | $CF_3$ | $CH_2cPr$ | Ph-3,5-$Me_2$ | |
| 151 | $CF_3$ | H | H | H | $CF_3$ | $CH_2cPr$ | Ph-3-Me | |
| 152 | $CF_3$ | H | H | H | $CF_3$ | $CH_2cPr$ | Ph-3-Me-4-F | |
| 153 | $CF_3$ | H | H | H | $CF_3$ | $CH_2cPr$ | Ph-3-Me-4-OMe | |
| 154 | $CF_3$ | H | H | H | $CF_3$ | $CH_2cPr$ | Ph-4-F | |
| 155 | $CF_3$ | H | H | H | $CF_3$ | $CH_2cPr$ | Ph-4-Me | |
| 156 | $CF_3$ | H | H | H | $CF_3$ | $CH_2cPr$ | Ph-4-OMe | $n_D^{22.6}$ 1.5031 |
| 157 | $CF_3$ | H | H | H | $CF_3$ | $CH_2cPr$ | Ph | 68–69 |
| 158 | $CF_3$ | H | H | H | $CF_3$ | $CH_2C\equiv CH$ | Ph-4-OMe | |
| 159 | $CF_3$ | H | H | H | $CF_3$ | $CH_2C\equiv Cl$ | Ph-4-OMe | |
| 160 | $CF_3$ | H | H | H | $CF_3$ | iPr | Ph-4-OMe | |
| 161 | $CF_3$ | H | H | H | $CF_3$ | nBu | Ph-4-OMe | |
| 162 | $CF_3$ | H | H | H | $CF_3$ | nPr | Ph-4-OMe | |
| 163 | $CF_3$ | H | H | H | $CF_3$ | tBu | Ph-4-OMe | |
| 164 | $CF_3$ | H | H | H | OMe | $CH_2CH=CH_2$ | Ph-4-OMe | |
| 165 | $CF_3$ | H | H | H | OMe | $CH(CH_3)CH=CH_2$ | Ph-4-OMe | |
| 166 | $CF_3$ | H | H | H | OMe | $CH_2CH=CHCl$ | Ph-4-OMe | |
| 167 | $CF_3$ | H | H | H | OMe | $CH_2CH=CCl_2$ | Ph-4-OMe | |
| 168 | $CF_3$ | H | H | H | OMe | $CH_2CH=CHCH_3$ | Ph-4-OMe | |
| 169 | $CF_3$ | H | H | H | OMe | Et | Ph-4-OMe | 95–96 |
| 170 | $CF_3$ | H | H | H | OMe | $CH_2CH_2Cl$ | Ph-4-OMe | |
| 171 | $CF_3$ | H | H | H | OMe | $CH_2CHF_2$ | Ph-4-OMe | |
| 172 | $CF_3$ | H | H | H | OMe | Me | Ph-4-OMe | |
| 173 | $CF_3$ | H | H | H | OMe | $CH_2C(Cl)=CH_2$ | Ph-4-OMe | |
| 174 | $CF_3$ | H | H | H | OMe | $CH_2C(CH_3)=CH_2$ | Ph-4-OMe | |
| 175 | $CF_3$ | H | H | H | OMe | $CH_2CN$ | Ph-4-OMe | |
| 176 | $CF_3$ | H | H | H | OMe | $CH_2OMe$ | Ph-4-OMe | |
| 177 | $CF_3$ | H | H | H | OMe | $CH_2cPr$ | 3-methyl-pyrazol-1-yl | |
| 178 | $CF_3$ | H | H | H | OMe | $CH_2cPr$ | 4-methyl-pyrazol-1-yl | |
| 179 | $CF_3$ | H | H | H | OMe | $CH_2cPr$ | pyrazol-1-yl | |
| 180 | $CF_3$ | H | H | H | OMe | $CH_2cPr$ | 3-methyl-2-thienyl | |
| 181 | $CF_3$ | H | H | H | OMe | $CH_2cPr$ | 4-methyl-2-thienyl | |
| 182 | $CF_3$ | H | H | H | OMe | $CH_2cPr$ | 5-methyl-2-thienyl | |
| 183 | $CF_3$ | H | H | H | OMe | $CH_2cPr$ | 2-thienyl | |
| 184 | $CF_3$ | H | H | H | OMe | $CH_2cPr$ | 4-methyl-3-thienyl | |
| 185 | $CF_3$ | H | H | H | OMe | $CH_2cPr$ | 5-methyl-3-thienyl | |
| 186 | $CF_3$ | H | H | H | OMe | $CH_2cPr$ | 3-thienyl | |
| 187 | $CF_3$ | H | H | H | OMe | $CH_2cPr$ | Ph-2,4-$F_2$ | |
| 188 | $CF_3$ | H | H | H | OMe | $CH_2cPr$ | Ph-2-F | |
| 189 | $CF_3$ | H | H | H | OMe | $CH_2cPr$ | Ph-2-F-3-Me | |
| 190 | $CF_3$ | H | H | H | OMe | $CH_2cPr$ | Ph-2-F-4-OMe | |
| 191 | $CF_3$ | H | H | H | OMe | $CH_2cPr$ | Ph-2-F-4-OMe-5-Me | |
| 192 | $CF_3$ | H | H | H | OMe | $CH_2cPr$ | Ph-2-F-5-Me | |
| 193 | $CF_3$ | H | H | H | OMe | $CH_2cPr$ | Ph-3,5-$Me_2$ | |
| 194 | $CF_3$ | H | H | H | OMe | $CH_2cPr$ | Ph-3-Me | |
| 195 | $CF_3$ | H | H | H | OMe | $CH_2cPr$ | Ph-3-Me-4-F | |
| 196 | $CF_3$ | H | H | H | OMe | $CH_2cPr$ | Ph-3-Me-4-OMe | |
| 197 | $CF_3$ | H | H | H | OMe | $CH_2cPr$ | Ph-4-F | |
| 198 | $CF_3$ | H | H | H | OMe | $CH_2cPr$ | Ph-4-Me | |
| 199 | $CF_3$ | H | H | H | OMe | $CH_2cPr$ | Ph-4-OMe | 92–93 |
| 200 | $CF_3$ | H | H | H | OMe | $CH_2cPr$ | Ph-3-Cl-4-OMe | |
| 201 | $CF_3$ | H | H | H | OMe | $CH_2cPr$ | Ph-3-Cl-4-OMe-5-Me | |
| 202 | $CF_3$ | H | H | H | OMe | $CH_2cPr$ | Ph | |
| 203 | $CF_3$ | H | H | H | OMe | $CH_2C\equiv CH$ | Ph-4-OMe | |
| 204 | $CF_3$ | H | H | H | OMe | $CH_2C\equiv Cl$ | Ph-4-OMe | |
| 205 | $CF_3$ | H | H | H | OMe | iPr | Ph-4-OMe | |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 206 | CF₃ | H | H | H | OMe | nBu | Ph-4-OMe | |
| 207 | CF₃ | H | H | H | OMe | nPr | Ph-4-OMe | |
| 208 | CF₃ | H | H | H | OMe | tBu | Ph-4-OMe | |
| 209 | CF₃ | H | H | H | SMe | Et | Ph-4-OMe | 89–90 |
| 210 | CF₃ | H | H | H | SMe | Me | Ph-4-OMe | |
| 211 | CF₃ | H | H | H | SMe | CH₂cPr | Ph-4-OMe | 73–75 |
| 212 | CF₃ | H | H | H | SMe | CH₂cPr | Ph | 106–109 |
| 213 | CF₃ | H | H | H | SMe | nBu | Ph-4-OMe | |
| 214 | CF₃ | H | H | H | SMe | tBu | Ph-4-OMe | |
| 215 | CF₃ | H | H | Cl | H | CH₂CH=CH₂ | Ph-4-OMe | |
| 216 | CF₃ | H | H | Cl | H | Et | Ph-4-OMe | |
| 217 | CF₃ | H | H | Cl | H | Me | Ph-4-OMe | |
| 218 | CF₃ | H | H | Cl | H | CH₂cPr | 3-methyl-pyrazol-1-yl | |
| 219 | CF₃ | H | H | Cl | H | CH₂cPr | 4-methyl-pyrazol-1-yl | |
| 220 | CF₃ | H | H | Cl | H | CH₂cPr | pyrazol-1-yl | |
| 221 | CF₃ | H | H | Cl | H | CH₂cPr | 3-methyl-2-thienyl | |
| 222 | CF₃ | H | H | Cl | H | CH₂cPr | 4-methyl-2-thienyl | |
| 223 | CF₃ | H | H | Cl | H | CH₂cPr | 5-methyl-2-thienyl | |
| 224 | CF₃ | H | H | Cl | H | CH₂cPr | 2-thienyl | |
| 225 | CF₃ | H | H | Cl | H | CH₂cPr | 4-methyl-3-thienyl | |
| 226 | CF₃ | H | H | Cl | H | CH₂cPr | 5-methyl-3-thienyl | |
| 227 | CF₃ | H | H | Cl | H | CH₂cPr | 3-thienyl | |
| 228 | CF₃ | H | H | Cl | H | CH₂cPr | Ph-4-OMe | |
| 229 | CF₃ | H | H | Cl | H | CH₂C≡CH | Ph-4-OMe | |
| 230 | CF₃ | H | H | Cl | H | iPr | Ph-4-OMe | |
| 231 | CF₃ | H | H | Cl | H | nBu | Ph-4-OMe | |
| 232 | CF₃ | H | H | Cl | H | nPr | Ph-4-OMe | |
| 233 | CF₃ | H | H | Cl | H | tBu | Ph-4-OMe | |
| 234 | CF₃ | H | H | Cl | F | CH₂CH=CH₂ | Ph-4-OMe | 81–83 |
| 235 | CF₃ | H | H | Cl | F | CH(CH₃)CH=CH₂ | Ph-4-OMe | |
| 236 | CF₃ | H | H | Cl | F | CH₂CH=CHCl | Ph-4-OMe | |
| 237 | CF₃ | H | H | Cl | F | CH₂CH=CCl₂ | Ph-4-OMe | |
| 238 | CF₃ | H | H | Cl | F | CH₂CH=CHCH₃ | Ph-4-OMe | |
| 239 | CF₃ | H | H | Cl | F | Et | Ph-4-OMe | 99–100 |
| 240 | CF₃ | H | H | Cl | F | CH₂CH₂Cl | Ph-4-OMe | $n_D^{24.0}$ 1.5301 |
| 241 | CF₃ | H | H | Cl | F | CH₂CH₂Cl | Ph | 90–91 |
| 242 | CF₃ | H | H | Cl | F | CH₂CH₂Cl | Ph-2-F-5-Me | $n_D^{24.0}$ 1.5241 |
| 243 | CF₃ | H | H | Cl | F | CH₂CHF₂ | Ph-4-OMe | |
| 244 | CF₃ | H | H | Cl | F | Me | Ph-4-OMe | |
| 245 | CF₃ | H | H | Cl | F | CH₂C(Cl)=CH₂ | Ph-4-OMe | |
| 246 | CF₃ | H | H | Cl | F | CH₂C(CH₃)=CH₂ | Ph-4-OMe | |
| 247 | CF₃ | H | H | Cl | F | CH₂CN | Ph-4-OMe | |
| 248 | CF₃ | H | H | Cl | F | CH₂OMe | Ph-4-OMe | |
| 249 | CF₃ | H | H | Cl | F | CH₂cPr | 3-tnethyl-pyrazol-1-yl | |
| 250 | CF₃ | H | H | Cl | F | CH₂cPr | 4-methyl-pyrazol-1-yl | |
| 251 | CF₃ | H | H | Cl | F | CH₂cPr | pyrazol-1-yl | |
| 252 | CF₃ | H | H | Cl | F | CH₂cPr | 3-methyl-2-thienyl | |
| 253 | CF₃ | H | H | Cl | F | CH₂cPr | 4-methyl-2-thienyl | |
| 254 | CF₃ | H | H | Cl | F | CH₂cPr | 5-methyl-2-thienyl | |
| 255 | CF₃ | H | H | Cl | F | CH₂cPr | 2-thienyl | 112–113 |
| 256 | CF₃ | H | H | Cl | F | CH₂cPr | 4-methyl-3-thienyl | |
| 257 | CF₃ | H | H | Cl | F | CH₂cPr | 5-methyl-3-thienyl | |
| 258 | CF₃ | H | H | Cl | F | CH₂cPr | 3-thienyl | 125–126 |
| 259 | CF₃ | H | H | Cl | F | CH₂cPr | Ph-2,4-F₂ | |
| 260 | CF₃ | H | H | Cl | F | CH₂cPr | Ph-2-F | 57–59 |
| 261 | CF₃ | H | H | Cl | F | CH₂cPr | Ph-2-F-3-Me | |
| 262 | CF₃ | H | H | Cl | F | CH₂cPr | Ph-2F-4-OMe | $n_D^{26.7}$ 1.5200 |
| 263 | CF₃ | H | H | Cl | F | CH₂cPr | Ph-2-F-4-OMe- | 73–74 |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 264 | CF₃ | H | H | Cl | F | CH₂cPr | Ph-2-F-5-Me | 60–62 |
| 265 | CF₃ | H | H | Cl | F | CH₂cPr | Ph-3,5-Me₂ | |
| 266 | CF₃ | H | H | Cl | F | CH₂cPr | Ph-3-Me | 92–93 |
| 267 | CF₃ | H | H | Cl | F | CH₂cPr | Ph-3-Me-4-F | 98–99 |
| 268 | CF₃ | H | H | Cl | F | CH₂cPr | Ph-3-Me-4-OMe | 86–87 |
| 269 | CF₃ | H | H | Cl | F | CH₂cPr | Ph-4-F | 94–95 |
| 270 | CF₃ | H | H | Cl | F | CH₂cPr | Ph-4-Me | 75–76 |
| 271 | CF₃ | H | H | Cl | F | CH₂cPr | Ph-4OMe | 98 |
| 272 | CF₃ | H | H | Cl | F | CH₂cPr | Ph | 112 |
| 273 | CF₃ | H | H | Cl | F | CH₂C≡CH | Ph | 54–58 |
| 274 | CF₃ | H | H | Cl | F | CH₂C≡CH | Ph-2-F-5-Me | 91–92 |
| 275 | CF₃ | H | H | Cl | F | CH₂C≡CH | Ph-4-OMe | 102–103 |
| 276 | CF₃ | H | H | Cl | F | CH₂C≡Cl | Ph-4-OMe | 112–114 |
| 277 | CF₃ | H | H | Cl | F | iPr | Ph-4-OMe | 124–125 |
| 278 | CF₃ | H | H | Cl | F | nBu | Ph-4-OMe | |
| 279 | CF₃ | H | H | Cl | F | nPr | Ph-4-OMe | 90–91 |
| 280 | CF₃ | H | H | Cl | F | tBu | Ph-4-OMe | |
| 281 | CF₃ | H | H | Cl | Cl | CH₂CH=CH₂ | Ph-4-OMe | 80–81 |
| 282 | CF₃ | H | H | Cl | Cl | CH(CH₃)CH=CH₂ | Ph-4-OMe | |
| 283 | CF₃ | H | H | Cl | Cl | CH₂CH=CHCl | Ph-4-OMe | |
| 284 | CF₃ | H | H | Cl | Cl | CH₂CH=CCl₂ | Ph-4-OMe | |
| 285 | CF₃ | H | H | Cl | Cl | CH₂CH=CHCH₃ | Ph-4-OMe | |
| 286 | CF₃ | H | H | Cl | Cl | Et | Ph | 123–124 |
| 287 | CF₃ | H | H | Cl | Cl | Et | Ph-2-F-5-Me | 78–81 |
| 288 | CF₃ | H | H | Cl | Cl | Et | Ph-4-OMe | 90–91 |
| 289 | CF₃ | H | H | Cl | Cl | CH₂CH₂Cl | Ph | 104–105 |
| 290 | CF₃ | H | H | Cl | Cl | CH₂CH₂Cl | Ph-2-F-5-Me | $n_D^{26.5}$ 1.5309 |
| 291 | CF₃ | H | H | Cl | Cl | CH₂CH₂Cl | Ph-4-OMe | |
| 292 | CF₃ | H | H | Cl | Cl | CH₂CHF₂ | Ph-4-OMe | |
| 293 | CF₃ | H | H | Cl | Cl | Me | Ph-4-OMe | 77–79 |
| 294 | CF₃ | H | H | Cl | Cl | CH₂C(Cl)=CH₂ | Ph-4-OMe | |
| 295 | CF₃ | H | H | Cl | Cl | CH₂C(CH₃)=CH₂ | Ph-4-OMe | |
| 296 | CF₃ | H | H | Cl | Cl | CH₂CN | Ph-4-OMe | |
| 297 | CF₃ | H | H | Cl | Cl | CH₂OMe | Ph-4-OMe | |
| 298 | CF₃ | H | H | Cl | Cl | CH₂cPr | 3-methyl-pyrazol-1-yl | |
| 299 | CF₃ | H | H | Cl | Cl | CH₂cPr | 4-methyl-pyrazoi-1-yl | |
| 300 | CF₃ | H | H | Cl | Cl | CH₂cPr | pyrazol-1-yl | |
| 301 | CF₃ | H | H | Cl | Cl | CH₂cPr | 3-methyl-2-thienyl | |
| 302 | CF₃ | H | H | Cl | Cl | CH₂cPr | 4-methyl-2-thienyl | |
| 303 | CF₃ | H | H | Cl | Cl | CH₂cPr | 5-methyl-2-thienyl | |
| 304 | CF₃ | H | H | Cl | Cl | CH₂cPr | 2-thienyl | 139–141 |
| 305 | CF₃ | H | H | Cl | Cl | CH₂cPr | 4-methyl-3-thienyl | |
| 306 | CF₃ | H | H | Cl | Cl | CH₂cPr | 5-methyl-3-thienyl | |
| 307 | CF₃ | H | H | Cl | Cl | CH₂cPr | 3-thienyl | 140–141 |
| 308 | CF₃ | H | H | Cl | Cl | CH₂cPr | Ph-2,4-F₂ | |
| 309 | CF₃ | H | H | Cl | Cl | CH₂cPr | Ph-2-F | $n_D^{23.0}$ 1.5404 |
| 310 | CF₃ | H | H | Cl | Cl | CH₂cPr | Ph-2-F-3-Me | |
| 311 | CF₃ | H | H | Cl | Cl | CH₂cPr | Ph-2-F-4-OMe | $n_D^{22.5}$ 1.5371 |
| 312 | CF₃ | H | H | Cl | Cl | CH₂cPr | Ph-2F-4-OMe-5-Me | $n_D^{23.5}$ 1.5287 |
| 313 | CF₃ | H | H | Cl | Cl | CH₂cPr | Ph-2-F-5-Me | 56–57 |
| 314 | CF₃ | H | H | Cl | Cl | CH₂cPr | Ph-3,5-Me₂ | |
| 315 | CF₃ | H | H | Cl | Cl | CH₂cPr | Ph-3-Me | 111–114 |
| 316 | CF₃ | H | H | Cl | Cl | CH₂cPr | Ph-3-Me-4-F | 113–114 |
| 317 | CF₃ | H | H | Cl | Cl | CH₂cPr | Ph-3-Me-4-OMe | |
| 318 | CF₃ | H | H | Cl | Cl | CH₂cPr | Ph-4-F | |
| 319 | CF₃ | H | H | Cl | Cl | CH₂cPr | Ph-4-Me | 93–95 |
| 320 | CF₃ | H | H | Cl | Cl | CH₂cPr | Ph-4-OMe | 97–98 |
| 321 | CF₃ | H | H | Cl | Cl | CH₂cPr | Ph | 134–135 |
| 322 | CF₃ | H | H | Cl | Cl | CH₂C≡CH | Ph | 96–98 |

TABLE 3-continued ($r^1, r^2 = H$)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 323 | $CF_3$ | H | H | Cl | Cl | $CH_2C\equiv CH$ | Ph-2-F-5-Me | 77–79 |
| 324 | $CF_3$ | H | H | Cl | Cl | $CH_2C\equiv CH$ | Ph-4-OMe | 94–96 |
| 325 | $CF_3$ | H | H | Cl | Cl | $CH_2C\equiv CI$ | Ph-4-OMe | |
| 326 | $CF_3$ | H | H | Cl | Cl | iPr | Ph-4-OMe | 123–124 |
| 327 | $CF_3$ | H | H | Cl | Cl | nBu | Ph-4-OMe | |
| 328 | $CF_3$ | H | H | Cl | Cl | nPr | Ph-4-OMe | 88–89 |
| 329 | $CF_3$ | H | H | Cl | Cl | tBu | Ph-4-OMe | |
| 330 | $CF_3$ | H | H | SMe | F | $CH_2cPr$ | Ph-4-OMe | 114–115 |
| 331 | $CF_3$ | H | H | OMe | F | $CH_2cPr$ | Ph-4-OMe | 125–126 |
| 332 | $CF_3$ | H | H | OMe | F | $CH_2cPr$ | Ph-4-OMe | 135–136 |
| 333 | $CF_3$ | H | H | Me | F | $CH_2cPr$ | Ph-4-OMe | 71–72 |
| 334 | $CF_3$ | H | F | H | H | Et | Ph-4-OMe | 70–72 |
| 335 | $CF_3$ | H | F | H | H | Me | Ph-4-OMe | |
| 336 | $CF_3$ | H | F | H | H | $CH_2cPr$ | Ph-4-OMe | 97–99 |
| 337 | $CF_3$ | H | F | H | H | $CH_2cPr$ | Ph | 117–119 |
| 338 | $CF_3$ | H | F | H | H | nBu | Ph-4-OMe | |
| 339 | $CF_3$ | H | F | H | H | tBu | Ph | |
| 340 | $CF_3$ | H | Cl | H | H | Et | Ph-4-OMe | 89–91 |
| 341 | $CF_3$ | H | Cl | H | H | Me | Ph-4-OMe | |
| 342 | $CF_3$ | H | Cl | H | H | $CH_2cPr$ | Ph-4-OMe | 97–99 |
| 343 | $CF_3$ | H | Cl | H | H | $CH_2cPr$ | Ph | 91–92 |
| 344 | $CF_3$ | H | Cl | H | H | nBu | Ph-4-OMe | |
| 345 | $CF_3$ | H | Cl | H | H | tBu | Ph | |
| 346 | $CF_3$ | Cl | H | H | F | $CH_2cPr$ | Ph-4-OMe | Oil, *1 |
| 347 | $CF_3$ | Cl | H | H | Cl | $CH_2cPr$ | 2-thienyl | 74 |
| 348 | $CF_3$ | Cl | H | H | Cl | $CH_2cPr$ | Ph-4-OMe | 100 |
| 349 | $CF_3$ | Cl | H | H | Cl | $CH_2cPr$ | Ph | 95–96 |
| 350 | $CF_3$ | H | H | F | F | $CH_2CH=CH_2$ | Ph-4-OMe | |
| 351 | $CF_3$ | H | H | F | F | Et | Ph | 81–83 |
| 352 | $CF_3$ | H | H | F | F | Et | Ph-2-F-5-Me | 79–80 |
| 353 | $CF_3$ | H | H | F | F | Et | Ph-4-OMe | 78–79 |
| 354 | $CF_3$ | H | H | F | F | $CH_2CH_2Cl$ | Ph | $n_D^{23.5}$ 1.5245 |
| 355 | $CF_3$ | H | H | F | F | $CH_2CH_2Cl$ | Ph-2-F-5-Me | |
| 356 | $CF_3$ | H | H | F | F | $CH_2CH_2Cl$ | Ph-4-OMe | |
| 357 | $CF_3$ | H | H | F | F | Me | Ph-4-OMe | |
| 358 | $CF_3$ | H | H | F | F | $CH_2OMe$ | Ph-4-OMe | |
| 359 | $CF_3$ | H | H | F | F | $CH_2cPr$ | 3-methyl-pyrazol-1-yl | |
| 360 | $CF_3$ | H | H | F | F | $CH_2cPr$ | 4-methyl-pyrazol-1-yl | |
| 361 | $CF_3$ | H | H | F | F | $CH_2cPr$ | pyrazol-1-yl | |
| 362 | $CF_3$ | H | H | F | F | $CH_2cPr$ | 3-methyl-2-thienyl | |
| 363 | $CF_3$ | H | H | F | F | $CH_2cPr$ | 4-methyl-2-thienyl | |
| 364 | $CF_3$ | H | H | F | F | $CH_2cPr$ | Ph-2-F | 56–58 |
| 365 | $CF_3$ | H | H | F | F | $CH_2cPr$ | Ph-2-F-3-Me | |
| 366 | $CF_3$ | H | H | F | F | $CH_2cPr$ | Ph-2F-4-OMe | |
| 367 | $CF_3$ | H | H | F | F | $CH_2cPr$ | Ph-2F-4-OMe-5-Me | 70–73 |
| 368 | $CF_3$ | H | H | F | F | $CH_2cPr$ | Ph-2F-5-Me | 67–69 |
| 369 | $CF_3$ | H | H | F | F | $CH_2cPr$ | Ph-3,5-Me$_2$ | |
| 370 | $CF_3$ | H | H | F | F | $CH_2cPr$ | Ph-3-Me | 70–72 |
| 371 | $CF_3$ | H | H | F | F | $CH_2cPr$ | Ph-3-Me-4-F | 51–53 |
| 372 | $CF_3$ | H | H | F | F | $CH_2cPr$ | Ph-3-Me-4-OMe | 56–57 |
| 373 | $CF_3$ | H | H | F | F | $CH_2cPr$ | Ph-4-F | 70–72 |
| 374 | $CF_3$ | H | H | F | F | $CH_2cPr$ | Ph-4-Me | 64–66 |
| 375 | $CF_3$ | H | H | F | F | $CH_2cPr$ | Ph-4-OMe | 73–74 |
| 376 | $CF_3$ | H | H | F | F | $CH_2cPr$ | Ph | 61–62 |
| 377 | $CF_3$ | H | H | F | F | $CH_2C\equiv CH$ | Ph | 76–78 |
| 378 | $CF_3$ | H | H | F | F | $CH_2C\equiv CH$ | Ph-2-F-5-Me | 84–86 |
| 379 | $CF_3$ | H | H | F | F | $CH_2C\equiv CH$ | Ph-4-OMe | 100–102 |
| 380 | $CF_3$ | H | H | F | F | $CH_2C\equiv CI$ | Ph-4-OMe | |
| 381 | $CF_3$ | H | H | F | F | iPr | Ph-4-OMe | 65–66 |
| 382 | $CF_3$ | H | H | F | F | nBu | Ph-4-OMe | |
| 383 | $CF_3$ | H | H | F | F | nPr | Ph-4-OMe | 67–69 |
| 384 | $CF_3$ | H | H | F | F | tBu | Ph-4-OMe | |

TABLE 3-continued (r$^1$, r$^2$ = H)

| No. | X$^1$ | X$^2$ | X$^3$ | X$^4$ | X$^5$ | R$^1$ | R$^2$ | Physical const. mp. (°C.) refractive index |
|---|---|---|---|---|---|---|---|---|
| 385 | CF$_3$ | H | H | F | F | CH$_2$cPr | 5-methyl-2-thienyl | |
| 386 | CF$_3$ | H | H | F | F | CH$_2$cPr | 2-thienyl | 69–71 |
| 387 | CF$_3$ | H | H | F | F | CH$_2$cPr | 4-methyl-3-thienyl | |
| 388 | CF$_3$ | H | H | F | F | CH$_2$cPr | 5-methyl-3-thienyl | |
| 389 | CF$_3$ | H | H | F | F | CH$_2$cPr | 3-thienyl | 79–81 |
| 390 | CF$_3$ | H | H | F | F | CH$_2$cPr | Ph-2,4-F$_2$ | |
| 391 | CF$_3$ | H | H | Cl | F | nPr | Ph | 113–114 |
| 392 | CF$_3$ | H | H | Cl | F | nPr | Ph-2-F-5-Me | 60–61 |
| 393 | CF$_3$ | H | H | Cl | F | iPr | Ph | 111–112 |
| 394 | CF$_3$ | H | H | Cl | F | iPr | Ph-2-F-5-Me | |
| 395 | CF$_3$ | H | H | Cl | F | CH$_2$CH=CH$_2$ | Ph | 107–108 |
| 396 | CF$_3$ | H | H | Cl | F | CH$_2$CH=CH$_2$ | Ph-2-F-5-Me | 68–70 |
| 397 | CF$_3$ | H | H | Cl | F | CH$_3$ | Ph | |
| 398 | CF$_3$ | H | H | Cl | F | CH$_3$ | Ph-2-F-5-Me | |
| 399 | CF$_3$ | H | H | Cl | F | CH$_2$C≡Cl | Ph | 90–91 |
| 400 | CF$_3$ | H | H | Cl | F | CH$_2$C≡Cl | Ph-2-F-5-Me | n$_D^{25.0}$ 1.5491 |
| 401 | CF$_3$ | H | H | Cl | F | CH$_2$CH$_3$ | Ph | 101–102 |
| 402 | CF$_3$ | H | H | Cl | F | CH$_2$CH$_3$ | Ph-2-F-5-Me | 60–62 |
| 403 | CF$_3$ | H | H | Cl | Cl | nPr | Ph | 128–129 |
| 404 | CF$_3$ | H | H | Cl | Cl | nPr | Ph-2-F-5-Me | n$_D^{24.0}$ 1.5212 |
| 405 | CF$_3$ | H | H | Cl | Cl | iPr | Ph | 125–127 |
| 406 | CF$_3$ | H | H | Cl | Cl | iPr | Ph-2-F-5-Me | n$_D^{24.7}$ 1.5245 |
| 407 | CF$_3$ | H | H | Cl | Cl | CH$_2$CH=CH$_2$ | Ph | 115–116 |
| 408 | CF$_3$ | H | H | Cl | Cl | CH$_2$CH=CH$_2$ | Ph-2-F-5-Me | 62–63 |
| 409 | CF$_3$ | H | H | Cl | Cl | CH$_3$ | Ph | 111–113 |
| 410 | CF$_3$ | H | H | Cl | Cl | CH$_3$ | Ph-2-F-5-Me | 80–81 |
| 411 | CF$_3$ | H | H | Cl | Cl | CH$_2$C≡Cl | Ph | |
| 412 | CF$_3$ | H | H | Cl | Cl | CH$_2$C≡Cl | Ph-2-F-5-Me | |
| 413 | CF$_3$ | H | H | F | F | nPr | Ph | 56–58 |
| 414 | CF$_3$ | H | H | F | F | nPr | Ph-2-F-5-Me | 38–40 |
| 415 | CF$_3$ | H | H | F | F | iPr | Ph | 81–82.5 |
| 416 | CF$_3$ | H | H | F | F | iPr | Ph-2-F-5-Me | |
| 417 | CF$_3$ | H | H | F | F | CH$_2$CH=CH$_2$ | Ph | |
| 418 | CF$_3$ | H | H | F | F | CH$_2$CH=CH$_2$ | Ph-2-F-5-Me | |
| 419 | CF$_3$ | H | H | F | F | CH$_3$ | Ph | |
| 420 | CF$_3$ | H | H | F | F | CH$_3$ | Ph-2-F-5-Me | |
| 421 | CF$_3$ | H | H | F | F | CH$_2$C≡Cl | Ph | |
| 422 | CF$_3$ | H | H | F | F | CH$_2$C≡Cl | Ph-2-F-5-Me | |
| 423 | CF$_3$ | H | H | F | Cl | CH$_2$CH=CH$_2$ | Ph | |
| 424 | CF$_3$ | H | H | F | Cl | CH$_2$CH=CH$_2$ | Ph-4-OMe | |
| 425 | CF$_3$ | H | H | F | Cl | CH$_2$CH=CH$_2$ | Ph-2-F-5-Me | |
| 426 | CF$_3$ | H | H | F | Cl | CH$_2$CH$_3$ | Ph | |
| 427 | CF$_3$ | H | H | F | Cl | CH$_2$CH$_3$ | Ph-4-OMe | |
| 428 | CF$_3$ | H | H | F | Cl | CH$_2$CH$_3$ | Ph-2-F-5-Me | |
| 429 | CF$_3$ | H | H | F | Cl | CH$_2$CH$_2$Cl | Ph | n$_D^{24.5}$ 1.5344 |
| 430 | CF$_3$ | H | H | F | Cl | CH$_2$CH$_2$Cl | Ph-4-OMe | n$_D^{24.5}$ 1.5294 |
| 431 | CF$_3$ | H | H | F | Cl | CH$_2$CH$_2$Cl | Ph-2-F-5-Me | |
| 432 | CF$_3$ | H | H | F | Cl | CH$_3$ | Ph | |
| 433 | CF$_3$ | H | H | F | Cl | CH$_3$ | Ph-4-OMe | |
| 434 | CF$_3$ | H | H | F | Cl | CH$_3$ | Ph-2-F-5-Me | |
| 435 | CF$_3$ | H | H | F | Cl | CH$_2$OMe | Ph-4-OMe | |
| 436 | CF$_3$ | H | H | F | Cl | CH$_2$cPr | 3-methyl-pyrazol-1-yl | |
| 437 | CF$_3$ | H | H | F | Cl | CH$_2$cPr | 4-methyl-pyrazol-1-yl | |
| 438 | CF$_3$ | H | H | F | Cl | CH$_2$cPr | pyrazol-1-yl | |
| 439 | CF$_3$ | H | H | F | Cl | CH$_2$cPr | 3-methyl-2-thienyl | |
| 440 | CF$_3$ | H | H | F | Cl | CH$_2$cPr | 4-methyl-2-thienyl | |
| 441 | CF$_3$ | H | H | F | Cl | CH$_2$cPr | 5-methyl-2-thienyl | |
| 442 | CF$_3$ | H | H | F | Cl | CH$_2$cPr | 2-thienyl | 104–106 |
| 443 | CF$_3$ | H | H | F | Cl | CH$_2$cPr | 4-methyl- | |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 444 | CF₃ | H | H | F | Cl | CH₂cPr | 3-thienyl | |
| | | | | | | | 5-methyl-3-thienyl | |
| 445 | CF₃ | H | H | F | Cl | CH₂cPr | 3-thienyl | 113–115 |
| 446 | CF₃ | H | H | F | Cl | CH₂cPr | Ph-2,4-F₂ | |
| 447 | CF₃ | H | H | F | Cl | CH₂cPr | Ph-2-F | $n_D^{23.8}$ 1.5262 |
| 448 | CF₃ | H | H | F | Cl | CH₂cPr | Ph-2-F-3-Me | |
| 449 | CF₃ | H | H | F | Cl | CH₂cPr | Ph-2-F-4-OMe | |
| 450 | CF₃ | H | H | F | Cl | CH₂cPr | Ph-2-F-4-OMe-5-Me | |
| 451 | CF₃ | H | H | F | Cl | CH₂cPr | Ph-2-F-5-Me | 62–63 |
| 452 | CF₃ | H | H | F | Cl | CH₂cPr | Ph-3,5-Me₂ | |
| 453 | CF₃ | H | H | F | Cl | CH₂cPr | Ph-3-Me | 96–98 |
| 454 | CF₃ | H | H | F | Cl | CH₂cPr | Ph-3-Me-4-F | 82–83 |
| 455 | CF₃ | H | H | F | Cl | CH₂cPr | Ph-3-Me-4-OMe | 72–73 |
| 456 | CF₃ | H | H | F | Cl | CH₂cPr | Ph-4-F | 76–77 |
| 457 | CF₃ | H | H | F | Cl | CH₂cPr | Ph-4-Me | 75–76 |
| 458 | CF₃ | H | H | F | Cl | CH₂cPr | Ph-4-OMe | 68–69 |
| 459 | CF₃ | H | H | F | Cl | CH₂cPr | Ph | 102–104 |
| 460 | CF₃ | H | H | F | Cl | CH₂C≡CH | Ph | |
| 461 | CF₃ | H | H | F | Cl | CH₂C≡CH | Ph-4-OMe | |
| 462 | CF₃ | H | H | F | Cl | CH₂C≡CH | Ph-2-F-5-Me | |
| 463 | CF₃ | H | H | F | Cl | CH₂C≡Cl | Ph-4-OMe | |
| 464 | CF₃ | H | H | F | Cl | iPr | Ph | |
| 465 | CF₃ | H | H | F | Cl | iPr | Ph-4-OMe | |
| 466 | CF₃ | H | H | F | Cl | iPr | Ph-2-F-5-Me | |
| 467 | CF₃ | H | H | F | Cl | nPr | Ph | |
| 468 | CF₃ | H | H | F | Cl | nPr | Ph-4-OMe | |
| 469 | CF₃ | H | H | F | Cl | nPr | Ph-2-F-5-Me | |
| 470 | CF₃ | H | H | F | Cl | nBu | Ph-4-OMe | |
| 471 | CF₃ | H | H | F | Cl | tBu | Ph-4-OMe | |
| 472 | CF₃ | H | H | CF₃ | Cl | CH₂CH=CH₂ | Ph | |
| 473 | CF₃ | H | H | CF₃ | Cl | CH₂CH=CH₂ | Ph-4-OMe | |
| 474 | CF₃ | H | H | CF₃ | Cl | CH₂CH=CH₂ | Ph-2-F-5-Me | |
| 475 | CF₃ | H | H | CF₃ | Cl | CH₂CH₃ | Ph | |
| 476 | CF₃ | H | H | CF₃ | Cl | CH₂CH₃ | Ph-4-OMe | |
| 477 | CF₃ | H | H | CF₃ | Cl | CH₂CH₃ | Ph-2-F-5-Me | |
| 478 | CF₃ | H | H | CF₃ | Cl | CH₂CH₂Cl | Ph | |
| 479 | CF₃ | H | H | CF₃ | Cl | CH₂CH₂Cl | Ph-4-OMe | |
| 480 | CF₃ | H | H | CF₃ | Cl | CH₂CH₂Cl | Ph-2-F-5-Me | |
| 481 | CF₃ | H | H | CF₃ | Cl | CH₃ | Ph | |
| 482 | CF₃ | H | H | CF₃ | Cl | CH₃ | Ph-4-OMe | |
| 483 | CF₃ | H | H | CF₃ | Cl | CH₃ | Ph-2-F-5-Me | |
| 484 | CF₃ | H | H | CF₃ | Cl | CH₂OMe | Ph-4-OMe | |
| 485 | CF₃ | H | H | CF₃ | Cl | CH₂cPr | 3-methyl-pyrazol-1-yl | |
| 486 | CF₃ | H | H | CF₃ | Cl | CH₂cPr | 4-methyl-pyrazol-1-yl | |
| 487 | CF₃ | H | H | CF₃ | Cl | CH₂cPr | pyrazol-1-yl | |
| 488 | CF₃ | H | H | CF₃ | Cl | CH₂cPr | 3-methyl-2-thienyl | |
| 489 | CF₃ | H | H | CF₃ | Cl | CH₂cPr | 4-methyl-2-thienyl | |
| 490 | CF₃ | H | H | CF₃ | Cl | CH₂cPr | 5-methyl-2-thienyl | |
| 491 | CF₃ | H | H | CF₃ | Cl | CH₂cPr | 2-thienyl | |
| 492 | CF₃ | H | H | CF₃ | Cl | CH₂cPr | 4-methyl-3-thienyl | |
| 493 | CF₃ | H | H | CF₃ | Cl | CH₂cPr | 5-methyl-3-thienyl | |
| 494 | CF₃ | H | H | CF₃ | Cl | CH₂cPr | 3-thienyl | |
| 495 | CF₃ | H | H | CF₃ | Cl | CH₂cPr | Ph-2,4-F₂ | |
| 496 | CF₃ | H | H | CF₃ | Cl | CH₂cPr | Ph-2-F | |
| 497 | CF₃ | H | H | CF₃ | Cl | CH₂cPr | Ph-2-F-3-Me | |
| 498 | CF₃ | H | H | CF₃ | Cl | CH₂cPr | Ph-2-F-4-OMe | |
| 499 | CF₃ | H | H | CF₃ | Cl | CH₂cPr | Ph-2-F-4-OMe-5-Me | |
| 500 | CF₃ | H | H | CF₃ | Cl | CH₂cPr | Ph-2-F-5-Me | |
| 501 | CF₃ | H | H | CF₃ | Cl | CH₂cPr | Ph-3,5-Me₂ | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 502 | $CF_3$ | H | H | $CF_3$ | Cl | $CH_2cPr$ | Ph-3-Me | |
| 503 | $CF_3$ | H | H | $CF_3$ | Cl | $CH_2cPr$ | Ph-3-Me-4-F | |
| 504 | $CF_3$ | H | H | $CF_3$ | Cl | $CH_2cPr$ | Ph-3-Me-4-OMe | |
| 505 | $CF_3$ | H | H | $CF_3$ | Cl | $CH_2cPr$ | Ph-4-F | |
| 506 | $CF_3$ | H | H | $CF_3$ | Cl | $CH_2cPr$ | Ph-4-Me | |
| 507 | $CF_3$ | H | H | $CF_3$ | Cl | $CH_2cPr$ | Ph-4-OMe | |
| 508 | $CF_3$ | H | H | $CF_3$ | Cl | $CH_2cPr$ | Ph | 65–67 |
| 509 | $CF_3$ | H | H | $CF_3$ | Cl | $CH_2C{\equiv}CH$ | Ph | |
| 510 | $CF_3$ | H | H | $CF_3$ | Cl | $CH_2C{\equiv}CH$ | Ph-4-OMe | |
| 511 | $CF_3$ | H | H | $CF_3$ | Cl | $CH_2C{\equiv}CH$ | Ph-2-F-5-Me | |
| 512 | $CF_3$ | H | H | $CF_3$ | Cl | $CH_2C{\equiv}Cl$ | Ph | |
| 513 | $CF_3$ | H | H | $CF_3$ | Cl | iPr | Ph | |
| 514 | $CF_3$ | H | H | $CF_3$ | Cl | iPr | Ph-4-OMe | |
| 515 | $CF_3$ | H | H | $CF_3$ | Cl | iPr | Ph-2-F-5-Me | |
| 516 | $CF_3$ | H | H | $CF_3$ | Cl | nPr | Ph | |
| 517 | $CF_3$ | H | H | $CF_3$ | Cl | nPr | Ph-4-OMe | |
| 518 | $CF_3$ | H | H | $CF_3$ | Cl | nPr | Ph-2-F-5-Me | |
| 519 | $CF_3$ | H | H | $CF_3$ | Cl | nBu | Ph-4-OMe | |
| 520 | $CF_3$ | H | H | $CF_3$ | Cl | tBu | Ph-4-OMe | |
| 521 | $CF_3$ | H | H | $CF_3$ | F | $CH_2CH{=}CH_2$ | Ph | |
| 522 | $CF_3$ | H | H | $CF_3$ | F | $CH_2CH{=}CH_2$ | Ph-4-OMe | |
| 523 | $CF_3$ | H | H | $CF_3$ | F | $CH_2CH{=}CH_2$ | Ph-2-F-5-Me | |
| 524 | $CF_3$ | H | H | $CF_3$ | F | $CH_2CH_3$ | Ph | |
| 525 | $CF_3$ | H | H | $CF_3$ | F | $CH_2CH_3$ | Ph-4-OMe | |
| 526 | $CF_3$ | H | H | $CF_3$ | F | $CH_2CH_3$ | Ph-2-F-5-Me | |
| 527 | $CF_3$ | H | H | $CF_3$ | F | $CH_2CH_2Cl$ | Ph | |
| 528 | $CF_3$ | H | H | $CF_3$ | F | $CH_2CH_2Cl$ | Ph-4-OMe | |
| 529 | $CF_3$ | H | H | $CF_3$ | F | $CH_2CH_2Cl$ | Ph-2-F-5-Me | |
| 530 | $CF_3$ | H | H | $CF_3$ | F | $CH_3$ | Ph | |
| 531 | $CF_3$ | H | H | $CF_3$ | F | $CH_3$ | Ph-4-OMe | |
| 532 | $CF_3$ | H | H | $CF_3$ | F | $CH_3$ | Ph-2-F-5-Me | |
| 533 | $CF_3$ | H | H | $CF_3$ | F | $CH_2OMe$ | Ph-4-OMe | |
| 534 | $CF_3$ | H | H | $CF_3$ | F | $CH_2cPr$ | 3-methyl-2-thienyl | |
| 535 | $CF_3$ | H | H | $CF_3$ | F | $CH_2cPr$ | 4-methyl-2-thienyl | |
| 536 | $CF_3$ | H | H | $CF_3$ | F | $CH_2cFr$ | 5-methyl-2-thienyl | |
| 537 | $CF_3$ | H | H | $CF_3$ | F | $CH_2cPr$ | 2-thienyl | |
| 538 | $CF_3$ | H | H | $CF_3$ | F | $CH_2cPr$ | 4-methyl-3-thienyl | |
| 539 | $CF_3$ | H | H | $CF_3$ | F | $CH_2cPr$ | 5-methyl-3-thienyl | |
| 540 | $CF_3$ | H | H | $CF_3$ | F | $CH_2cPr$ | 3-thienyl | |
| 541 | $CF_3$ | H | H | $CF_3$ | F | $CH_2cPr$ | 4-methyl-3-thienyl | |
| 542 | $CF_3$ | H | H | $CF_3$ | F | $CH_2cPr$ | 5-methyl-3-thienyl | |
| 543 | $CF_3$ | H | H | $CF_3$ | F | $CH_2cPr$ | 3-thienyl | |
| 544 | $CF_3$ | H | H | $CF_3$ | F | $CH_2cPr$ | Ph-2,4-$F_2$ | |
| 545 | $CF_3$ | H | H | $CF_3$ | F | $CH_2cPr$ | Ph-2-F | |
| 546 | $CF_3$ | H | H | $CF_3$ | F | $CH_2cPr$ | Ph-2-F-3-Me | |
| 547 | $CF_3$ | H | H | $CF_3$ | F | $CH_2cPr$ | Ph-2-F-4-OMe | |
| 548 | $CF_3$ | H | H | $CF_3$ | F | $CH_2cPr$ | Ph-2-F-4-OMe-5-Me | |
| 549 | $CF_3$ | H | H | $CF_3$ | F | $CH_2cPr$ | Ph-2-F-5-Me | |
| 550 | $CF_3$ | H | H | $CF_3$ | F | $CH_2cPr$ | Ph-3,5-$Me_2$ | |
| 551 | $CF_3$ | H | H | $CF_3$ | F | $CH_2cPr$ | Ph-3-Me | |
| 552 | $CF_3$ | H | H | $CF_3$ | F | $CH_2cPr$ | Ph-3-Me-4-F | |
| 553 | $CF_3$ | H | H | $CF_3$ | F | $CH_2cPr$ | Ph-3-Me-4-OMe | |
| 554 | $CF_3$ | H | H | $CF_3$ | F | $CH_2cPr$ | Ph-4-F | |
| 555 | $CF_3$ | H | H | $CF_3$ | F | $CH_2cPr$ | Ph-4-Me | |
| 556 | $CF_3$ | H | H | $CF_3$ | F | $CH_2cPr$ | Ph-4-OMe | |
| 557 | $CF_3$ | H | H | $CF_3$ | F | $CH_2cPr$ | Ph | |
| 558 | $CF_3$ | H | H | $CF_3$ | F | $CH_2C{\equiv}CH$ | Ph | |
| 559 | $CF_3$ | H | H | $CF_3$ | F | $CH_2C{\equiv}CH$ | Ph-4-OMe | |
| 560 | $CF_3$ | H | H | $CF_3$ | F | $CH_2C{\equiv}CH$ | Ph-2-F-5-Me | |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 561 | CF₃ | H | H | CF₃ | F | CH₂C≡CI | Ph-4-OMe | |
| 562 | CF₃ | H | H | CF₃ | F | iPr | Ph | |
| 563 | CF₃ | H | H | CF₃ | F | iPr | Ph-4-OMe | |
| 564 | CF₃ | H | H | CF₃ | F | iPr | Ph-2-F-5-Me | |
| 565 | CF₃ | H | H | CF₃ | F | nPr | Ph | |
| 566 | CF₃ | H | H | CF₃ | F | nPr | Ph-4-OMe | |
| 567 | CF₃ | H | H | CF₃ | F | nPr | Ph-2-F-5-Me | |
| 568 | CF₃ | H | H | CF₃ | F | nBu | Ph-4-OMe | |
| 569 | CF₃ | H | H | CF₃ | F | tBu | Ph-4-OMe | |
| 570 | CF₃ | F | H | H | Cl | CH₂cPr | Ph | |
| 571 | CF₃ | F | H | H | Cl | CH₂cPr | Ph-4-OMe | |
| 572 | CF₃ | F | H | H | Cl | CH₂cPr | Ph-2-F-5-Me | |
| 573 | CF₃ | F | H | H | F | CH₂cPr | Ph | |
| 574 | CF₃ | F | H | H | F | CH₂cPr | Ph-4-OMe | |
| 575 | CF₃ | F | H | H | F | CH₂cPr | Ph-2-F-5-Me | |
| 576 | CF₃ | CF₃ | H | H | Cl | CH₂cPr | Ph | |
| 577 | CF₃ | CF₃ | H | H | Cl | CH₂cPr | Ph-4-OMe | |
| 578 | CF₃ | CF₃ | H | H | Cl | CH₂cPr | Ph-2-F-5-Me | |
| 579 | CF₃ | CF₃ | H | H | F | CH₂cPr | Ph | |
| 580 | CF₃ | CF₃ | H | H | F | CH₂cPr | Ph-4-OMe | |
| 581 | CF₃ | CF₃ | H | H | F | CH₂cPr | Ph-2-F-5-Me | |
| 582 | CF₃ | Cl | H | H | CF₃ | CH₂cPr | Ph | |
| 583 | CF₃ | Cl | H | H | CF₃ | CH₂cPr | Ph-4-OMe | |
| 584 | CF₃ | Cl | H | H | CF₃ | CH₂cPr | Ph-2-F-5-Me | |
| 585 | CF₃ | F | H | H | CF₃ | CH₂cPr | Ph | |
| 586 | CF₃ | F | H | H | CF₃ | CH₂cPr | Ph-4-OMe | |
| 587 | CF₃ | F | H | H | CF₃ | CH₂cPr | Ph-2-F-5-Me | |
| 588 | CF₃ | CF₃ | H | H | CF₃ | CH₂cPr | Ph | |
| 589 | CF₃ | CF₃ | H | H | CF₃ | CH₂cPr | Ph-4-OMe | |
| 590 | CF₃ | CF₃ | H | H | CF₃ | CH₂cPr | Ph-2-F-5-Me | |
| 591 | CF₃ | H | H | H | CH₃ | CH₂cPr | Ph | |
| 592 | CF₃ | H | H | H | CH₃ | CH₂cPr | Ph-4-OMe | |
| 593 | CF₃ | H | H | H | CH₃ | CH₂cPr | Ph-2-F-5-Me | |
| 594 | CF₃ | H | H | F | CH₃ | CH₂cPr | Ph | |
| 595 | CF₃ | H | H | F | CH₃ | CH₂cPr | Ph-4-OMe | |
| 596 | CF₃ | H | H | F | CH₃ | CH₂cPr | Ph-2-F-5-Me | |
| 597 | CF₃ | H | H | Cl | CH₃ | CH₂cPr | Ph | |
| 598 | CF₃ | H | H | Cl | CH₃ | CH₂cPr | Ph-4-OMe | |
| 599 | CF₃ | H | H | Cl | CH₃ | CH₂cPr | Ph-2-F-5-Me | |
| 600 | CF₃ | F | H | F | F | CH₂cPr | Ph | |
| 601 | CF₃ | F | H | F | F | CH₂cPr | Ph-4-OMe | |
| 602 | CF₃ | F | H | F | F | CH₂cPr | Ph-2-F-5-Me | |
| 603 | CF₃ | F | H | F | Cl | CH₂cPr | Ph | |
| 604 | CF₃ | F | H | F | Cl | CH₂cPr | Ph-4-OMe | |
| 605 | CF₃ | F | H | F | Cl | CH₂cPr | Ph-2-F-5-Me | |
| 606 | CF₃ | F | H | Cl | F | CH₂cPr | Ph | |
| 607 | CF₃ | F | H | Cl | F | CH₂cPr | Ph-4-OMe | |
| 608 | CF₃ | F | H | Cl | F | CH₂cPr | Ph-2-F-5-Me | |
| 609 | CF₃ | F | H | Cl | Cl | CH₂cPr | Ph | |
| 610 | CF₃ | F | H | Cl | Cl | CH₂cPr | Ph-4-OMe | |
| 611 | CF₃ | F | H | Cl | Cl | CH₂cPr | Ph-2-F-5-Me | |
| 612 | CF₃ | Cl | H | F | F | CH₂cPr | Ph | |
| 613 | CF₃ | Cl | H | F | F | CH₂cPr | Ph-4-OMe | |
| 614 | CF₃ | Cl | H | F | F | CH₂cPr | Ph-2-F-5-Me | |
| 615 | CF₃ | Cl | H | F | Cl | CH₂cPr | Ph | |
| 616 | CF₃ | Cl | H | F | Cl | CH₂cPr | Ph-4-OMe | |
| 617 | CF₃ | Cl | H | F | Cl | CH₂cPr | Ph-2-F-5-Me | |
| 618 | CF₃ | Cl | H | Cl | F | CH₂cPr | Ph | |
| 619 | CF₃ | Cl | H | Cl | F | CH₂cPr | Ph-4-OMe | |
| 620 | CF₃ | Cl | H | Cl | F | CH₂cPr | Ph-2-F-5-Me | |
| 621 | CF₃ | Cl | H | Cl | Cl | CH₂cPr | Ph | |
| 622 | CF₃ | Cl | H | Cl | Cl | CH₂cPr | Ph-4-OMe | |
| 623 | CF₃ | Cl | H | Cl | Cl | CH₂cPr | Ph-2-F-5-Me | |
| 624 | CF₃ | Cl | H | Cl | CF₃ | CH₂cPr | Ph | |
| 625 | CF₃ | Cl | H | F | CF₃ | CH₂cPr | Ph | |
| 626 | CF₃ | F | H | Cl | CF₃ | CH₂cPr | Ph | |
| 627 | CF₃ | F | H | F | CF₃ | CH₂cPr | Ph | |
| 628 | CF₃ | CF₃ | H | Cl | Cl | CH₂cPr | Ph | |
| 629 | CF₃ | CF₃ | H | Cl | F | CH₂cPr | Ph | |
| 630 | CF₃ | CF₃ | H | F | Cl | CH₂cPr | Ph | |
| 631 | CF₃ | CF₃ | H | F | F | CH₂cPr | Ph | |
| 632 | CF₃ | Cl | H | CF₃ | Cl | CH₂cPr | Ph | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 633 | $CF_3$ | F | H | $CF_3$ | Cl | $CH_2cPr$ | Ph | |
| 634 | $CF_3$ | Cl | H | $CF_3$ | F | $CH_2cPr$ | Ph | |
| 635 | $CF_3$ | F | H | $CF_3$ | F | $CH_2cPr$ | Ph | |
| 636 | $CF_3$ | $CF_3$ | H | Cl | $CF_3$ | $CH_2cPr$ | Ph | |
| 637 | $CF_3$ | $CF_3$ | H | F | $CF_3$ | $CH_2cPr$ | Ph | |
| 638 | $CF_3$ | $CF_3$ | H | $CF_3$ | $CF_3$ | $CH_2cPr$ | Ph | |
| 639 | $CF_3$ | F | F | F | F | $CH_2cPr$ | Ph | |
| 640 | $CF_3$ | F | F | F | Cl | $CH_2cPr$ | Ph | |
| 641 | $CF_3$ | F | F | Cl | F | $CH_2cPr$ | Ph | |
| 642 | $CF_3$ | F | F | Cl | Cl | $CH_2cPr$ | Ph | |
| 643 | $CF_3$ | Cl | H | Cl | $CF_3$ | $CH_2cPr$ | Ph-4-OMe | |
| 644 | $CF_3$ | Cl | H | F | $CF_3$ | $CH_2cPr$ | Ph-4-OMe | |
| 645 | $CF_3$ | F | H | Cl | $CF_3$ | $CH_2cPr$ | Ph-4-OMe | |
| 646 | $CF_3$ | F | H | F | $CF_3$ | $CH_2cPr$ | Ph-4-OMe | |
| 647 | $CF_3$ | $CF_3$ | H | Cl | Cl | $CH_2cPr$ | Ph-4-OMe | |
| 648 | $CF_3$ | $CF_3$ | H | Cl | F | $CH_2cPr$ | Ph-4-OMe | |
| 649 | $CF_3$ | $CF_3$ | H | F | Cl | $CH_2cPr$ | Ph-4-OMe | |
| 650 | $CF_3$ | $CF_3$ | H | F | F | $CH_2cPr$ | Ph-4-OMe | |
| 651 | $CF_3$ | Cl | H | $CF_3$ | Cl | $CH_2cPr$ | Ph-4-OMe | |
| 652 | $CF_3$ | F | H | $CF_3$ | Cl | $CH_2cPr$ | Ph-4-OMe | |
| 653 | $CF_3$ | Cl | H | $CF_3$ | F | $CH_2cPr$ | Ph-4-OMe | |
| 654 | $CF_3$ | F | H | $CF_3$ | F | $CH_2cPr$ | Ph-4-OMe | |
| 655 | $CF_3$ | $CF_3$ | H | Cl | $CF_3$ | $CH_2cPr$ | Ph-4-OMe | |
| 656 | $CF_3$ | $CF_3$ | H | F | $CF_3$ | $CH_2cPr$ | Ph-4-OMe | |
| 657 | $CF_3$ | $CF_3$ | H | $CF_3$ | $CF_3$ | $CH_2cPr$ | Ph-4-OMe | |
| 658 | $CF_3$ | F | F | F | F | $CH_2cPr$ | Ph-4-OMe | |
| 659 | $CF_3$ | F | F | F | Cl | $CH_2cPr$ | Ph-4-OMe | |
| 660 | $CF_3$ | F | F | Cl | F | $CH_2cPr$ | Ph-4-OMe | |
| 661 | $CF_3$ | F | F | Cl | Cl | $CH_2cPr$ | Ph-4-OMe | |
| 662 | $CF_3$ | H | H | H | F | $CH_2$-1-F-cPr | Ph | |
| 663 | $CF_3$ | H | H | H | F | $CH_2$-2-F-cPr | Ph | |
| 664 | $CF_3$ | H | H | H | F | $CH_2$-2-$F_2$-cPr | Ph | |
| 665 | $CF_3$ | H | H | H | F | $CH_2$-1-F-cPr | Ph-4-OMe | |
| 666 | $CF_3$ | H | H | H | F | $CH_2$-2-F-cPr | Ph-4-OMe | |
| 667 | $CF_3$ | H | H | H | F | $CH_2$-2-$F_2$-cPr | Ph-4-OMe | |
| 668 | $CF_3$ | H | H | Cl | Cl | $CH_2$-1-F-cPr | Ph | |
| 669 | $CF_3$ | H | H | Cl | Cl | $CH_2$-2-F-cPr | Ph | |
| 670 | $CF_3$ | H | H | Cl | Cl | $CH_2$-2-$F_2$-cPr | Ph | |
| 671 | $CF_3$ | H | H | Cl | Cl | $CH_2$-1-F-cPr | Ph-4-OMe | |
| 672 | $CF_3$ | H | H | Cl | Cl | $CH_2$-2-F-cPr | Ph-4-OMe | |
| 673 | $CF_3$ | H | H | Cl | Cl | $CH_2$-2-$F_2$-cPr | Ph-4-OMe | |
| 674 | $CF_3$ | H | H | Cl | F | $CH_2$-1-F-cPr | Ph | |
| 675 | $CF_3$ | H | H | Cl | F | $CH_2$-2-F-cPr | Ph | |
| 676 | $CF_3$ | H | H | Cl | F | $CH_2$-2-$F_2$-cPr | Ph | |
| 677 | $CF_3$ | H | H | Cl | F | $CH_2$-1-F-cPr | Ph-4-OMe | |
| 678 | $CF_3$ | H | H | Cl | F | $CH_2$-2-F-cPr | Ph-4-OMe | |
| 679 | $CF_3$ | H | H | Cl | F | $CH_2$-2-$F_2$-cPr | Ph-4-OMe | |
| 680 | $CF_3$ | H | H | F | Cl | $CH_2$-1-F-cPr | Ph | |
| 681 | $CF_3$ | H | H | F | Cl | $CH_2$-2-F-cPr | Ph | |
| 682 | $CF_3$ | H | H | F | Cl | $CH_2$-2-$F_2$-cPr | Ph | |
| 683 | $CF_3$ | H | H | F | Cl | $CH_2$-1-F-cPr | Ph-4-OMe | |
| 684 | $CF_3$ | H | H | F | Cl | $CH_2$-2-F-cPr | Ph-4-OMe | |
| 685 | $CF_3$ | H | H | F | Cl | $CH_2$-2-$F_2$-cPr | Ph-4-OMe | |
| 686 | $CF_3$ | H | H | F | F | $CH_2$-1-F-cPr | Ph | |
| 687 | $CF_3$ | H | H | F | F | $CH_2$-2-F-cPr | Ph | |
| 688 | $CF_3$ | H | H | F | F | $CH_2$-2-$F_2$-cPr | Ph | |
| 689 | $CF_3$ | H | H | F | F | $CH_2$-1-F-cPr | Ph-4-OMe | |
| 690 | $CF_3$ | H | H | F | F | $CH_2$-2-F-cPr | Ph-4-OMe | |
| 691 | $CF_3$ | H | H | F | F | $CH_2$-2-$F_2$-cPr | Ph-4-OMe | |
| 692 | $CF_3$ | H | H | H | Br | $CH_2CH_3$ | Ph | |
| 693 | $CF_3$ | H | H | H | Br | $CH_2CH_3$ | Ph-4-OMe | |
| 694 | $CF_3$ | H | H | H | Br | $CH_2$-cPr | Ph | $n_D^{23.5}$ 1.5343 |
| 695 | $CF_3$ | H | H | H | Br | $CH_2$-cPr | Ph-4-OMe | $n_D^{23.5}$ 1.5330 |
| 696 | $CF_3$ | H | H | H | Br | $CH_2$-cPr | Ph-2-F-5-Me | |
| 697 | $CF_3$ | H | H | F | Br | $CH_2CH_3$ | Ph | |
| 698 | $CF_3$ | H | H | F | Br | $CH_2CH_3$ | Ph-4-OMe | |
| 699 | $CF_3$ | H | H | F | Br | $CH_2$-cPr | Ph | 114–115 |
| 700 | $CF_3$ | H | H | F | Br | $CH_2$-cPr | Ph-4-OMe | $n_D^{23.1}$ 1.5304 |
| 701 | $CF_3$ | H | H | F | Br | $CH_2$-cPr | Ph-4-F | 81–82 |
| 702 | $CF_3$ | H | H | Cl | Br | $CH_2CH_3$ | Ph | |
| 703 | $CF_3$ | H | H | Cl | Br | $CH_2CH_3$ | Ph-4-OMe | |
| 704 | $CF_3$ | H | H | Cl | Br | $CH_2$-cPr | Ph | |
| 705 | $CF_3$ | H | H | Cl | Br | $CH_2$-cPr | Ph-4-OMe | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 706 | CF$_3$ | H | H | Cl | Br | CH$_2$-cPr | Ph-2-F-5-Me | |
| 707 | CF$_3$ | H | H | Br | F | CH$_2$CH$_3$ | Ph | |
| 708 | CF$_3$ | H | H | Br | F | CH$_2$CH$_3$ | Ph-4-OMe | |
| 709 | CF$_3$ | H | H | Br | F | CH$_2$-cPr | Ph | |
| 710 | CF$_3$ | H | H | Br | F | CH$_2$-cPr | Ph-4-OMe | |
| 711 | CF$_3$ | H | H | Br | F | CH$_2$-cPr | Ph-2-F-5-Me | |
| 712 | CF$_3$ | H | H | Br | Cl | CH$_2$CH$_3$ | Ph | |
| 713 | CF$_3$ | H | H | Br | Cl | CH$_2$CH$_3$ | Ph-4-OMe | |
| 714 | CF$_3$ | H | H | Br | Cl | CH$_2$-cPr | Ph | |
| 715 | CF$_3$ | H | H | Br | Cl | CH$_2$-cPr | Ph-4-OMe | |
| 716 | CF$_3$ | H | H | Br | Cl | CH$_2$-cPr | Ph-2-F-5-Me | |
| 717 | CF$_3$ | H | H | F | H | CH$_2$CH$_3$ | Ph | |
| 718 | CF$_3$ | H | H | F | H | CH$_2$CH$_3$ | Ph-4-OMe | |
| 719 | CF$_3$ | H | H | F | H | CH$_2$-cPr | Ph | 91–92 |
| 720 | CF$_3$ | H | H | F | H | CH$_2$-cPr | Ph-4-OMe | 109–110 |
| 721 | CF$_3$ | H | H | F | H | CH$_2$-cPr | Ph-2-F-5-Me | |
| 722 | CF$_3$ | H | H | Cl | H | CH$_2$CH$_3$ | Ph | |
| 723 | CF$_3$ | H | H | F | H | CH$_2$-cPr | Ph-2-F | 94–95 |
| 724 | CF$_3$ | H | H | Cl | H | CH$_2$-cPr | Ph | 99–100 |
| 725 | CF$_3$ | H | H | F | H | CH$_2$-cPr | Ph-4-F | 110–111 |
| 726 | CF$_3$ | H | H | Cl | H | CH$_2$-cPr | Ph-2-F-5-Me | |
| 727 | CF$_3$ | H | H | H | I | CH$_2$CH$_3$ | Ph | |
| 728 | CF$_3$ | H | H | H | I | CH$_2$CH$_3$ | Ph-4-OMe | |
| 729 | CF$_3$ | H | H | H | I | CH$_2$-cPr | Ph | |
| 730 | CF$_3$ | H | H | H | I | CH$_2$-cPr | Ph-4-OMe | |
| 731 | CF$_3$ | H | H | H | I | CH$_2$-cPr | Ph-2-F-5-Me | |
| 732 | CF$_3$ | H | H | Cl | Cl | CH$_2$-cHxe-3 | Ph | 106–107 |
| 733 | CF$_3$ | H | H | Cl | Cl | CH$_2$-cHex-3,4-Br$_2$ | Ph | 124–125 |
| 734 | CF$_3$ | H | H | Cl | Cl | CH$_2$-cHex | Ph | 106–109 |
| 735 | C$_2$F$_5$ | H | H | F | F | CH$_2$-cPr | Ph | |
| 736 | C$_2$F$_5$ | H | H | F | F | CH$_2$-cPr | Ph-4-OMe | |
| 737 | C$_2$F$_5$ | H | H | F | F | CH$_2$-cPr | Ph-2-F-5-Me | |
| 738 | C$_2$F$_5$ | H | H | F | F | CH$_2$CH$_2$Cl | Ph | |
| 739 | C$_2$F$_5$ | H | H | F | F | CH$_2$CH$_3$ | Ph | |
| 740 | C$_2$F$_5$ | H | H | F | F | CH$_2$C≡CH | Ph | |
| 741 | C$_2$F$_5$ | H | H | Cl | Cl | CH$_2$-cPr | Ph | |
| 742 | C$_2$F$_5$ | H | H | Cl | Cl | CH$_2$-cPr | Ph-4-OMe | |
| 743 | C$_2$F$_5$ | H | H | Cl | Cl | CH$_2$-cPr | Ph-2-F-5-Me | |
| 744 | C$_2$F$_5$ | H | H | Cl | Cl | CH$_2$CH$_2$Cl | Ph | |
| 745 | C$_2$F$_5$ | H | H | Cl | Cl | CH$_2$CH$_3$ | Ph | |
| 746 | C$_2$F$_5$ | H | H | Cl | Cl | CH$_2$C≡CH | Ph | |
| 747 | C$_2$F$_5$ | H | H | F | Cl | CH$_2$-cPr | Ph | |
| 748 | C$_2$F$_5$ | H | H | F | Cl | CH$_2$-cPr | Ph-4-OMe | |
| 749 | C$_2$F$_5$ | H | H | F | Cl | CH$_2$-cPr | Ph-2-F-5-Me | |
| 750 | C$_2$F$_5$ | H | H | F | Cl | CH$_2$CH$_2$Cl | Ph | |
| 751 | C$_2$F$_5$ | H | H | F | Cl | CH$_2$CH$_3$ | Ph | |
| 752 | C$_2$F$_5$ | H | H | F | Cl | CH$_2$C≡CH | Ph | |
| 753 | C$_2$F$_5$ | H | H | Cl | F | CH$_2$-cPr | Ph | |
| 754 | C$_2$F$_5$ | H | H | Cl | F | CH$_2$-cPr | Ph-4-OMe | |
| 755 | C$_2$F$_5$ | H | H | Cl | F | CH$_2$-cPr | Ph-2-F-5-Me | |
| 756 | C$_2$F$_5$ | H | H | Cl | F | CH$_2$CH$_2$Cl | Ph | |
| 757 | C$_2$F$_5$ | H | H | Cl | F | CH$_2$CH$_3$ | Ph | |
| 758 | C$_2$F$_5$ | H | H | Cl | F | CH$_2$≡CH | Ph | |
| 759 | CCl$_3$ | H | H | F | F | CH$_2$-cPr | Ph | |
| 760 | CCl$_3$ | H | H | F | F | CH$_2$-cPr | Ph-4-OMe | |
| 761 | CCl$_3$ | H | H | F | F | CH$_2$-cPr | Ph-2-F-5-Me | |
| 762 | CCl$_3$ | H | H | F | F | CH$_2$CH$_2$Cl | Ph | |
| 763 | CCl$_3$ | H | H | F | F | CH$_2$CH$_3$ | Ph | |
| 764 | CCl$_3$ | H | H | F | F | CH$_2$C≡CH | Ph | |
| 765 | CCl$_3$ | H | H | Cl | Cl | CH$_2$-cPr | Ph | |
| 766 | CCl$_3$ | H | H | Cl | Cl | CH$_2$-cPr | Ph-4-OMe | |
| 767 | CCl$_3$ | H | H | Cl | Cl | CH$_2$-cPr | Ph-2-F-5-Me | |
| 768 | CCl$_3$ | H | H | Cl | Cl | CH$_2$CH$_2$Cl | Ph | |
| 769 | CCl$_3$ | H | H | Cl | Cl | CH$_2$CH$_3$ | Ph | |
| 770 | CCl$_3$ | H | H | Cl | Cl | CH$_2$C≡CH | Ph | |
| 771 | CCl$_3$ | H | H | F | Cl | CH$_2$-cPr | Ph | |

TABLE 3-continued ($r^1$, $r^2$ = H)

| No. | $X^1$ | $X^2$ | $X^3$ | $X^4$ | $X^5$ | $R^1$ | $R^2$ | Physical const. mp. (°C.) refractive index |
|---|---|---|---|---|---|---|---|---|
| 772 | $CCl_3$ | H | H | F | Cl | $CH_2$-cPr | Ph-4-OMe | |
| 773 | $CCl_3$ | H | H | F | Cl | $CH_2$-cPr | Ph-2-F-5-Me | |
| 774 | $CCl_3$ | H | H | F | Cl | $CH_2CH_2Cl$ | Ph | |
| 775 | $CCl_3$ | H | H | F | Cl | $CH_2CH_3$ | Ph | |
| 776 | $CCl_3$ | H | H | F | Cl | $CH_2C\equiv CH$ | Ph | |
| 777 | $CCl_3$ | H | H | Cl | F | $CH_2$-cPr | Ph | |
| 778 | $CCl_3$ | H | H | Cl | F | $CH_2$-cPr | Ph-4-OMe | |
| 779 | $CCl_3$ | H | H | Cl | F | $CH_2$-cPr | Ph-2-F-5-Me | |
| 780 | $CCl_3$ | H | H | Cl | F | $CH_2CH_2Cl$ | Ph | |
| 781 | $CCl_3$ | H | H | Cl | F | $CH_2CH_3$ | Ph | |
| 782 | $CCl_3$ | H | H | Cl | F | $CH_2C\equiv CH$ | Ph | |
| 783 | $CHF_2$ | H | H | F | F | $CH_2$-cPr | Ph | |
| 784 | $CHF_2$ | H | H | F | F | $CH_2$-cPr | Ph-4-OMe | |
| 785 | $CHF_2$ | H | H | F | F | $CH_2$-cPr | Ph-2-F-5-Me | |
| 786 | $CHF_2$ | H | H | F | F | $CH_2CH_2Cl$ | Ph | |
| 787 | $CHF_2$ | H | H | F | F | $CH_2CH_3$ | Ph | |
| 788 | $CHF_2$ | H | H | F | F | $CH_2C\equiv CH$ | Ph | |
| 789 | $CHF_2$ | H | H | Cl | Cl | $CH_2$-cPr | Ph | |
| 790 | $CHF_2$ | H | H | Cl | Cl | $CH_2$-cPr | Ph-4-OMe | |
| 791 | $CHF_2$ | H | H | Cl | Cl | $CH_2$-cPr | Ph-2-F-5-Me | |
| 792 | $CHF_2$ | H | H | Cl | Cl | $CH_2CH_2Cl$ | Ph | |
| 793 | $CHF_2$ | H | H | Cl | Cl | $CH_2CH_3$ | Ph | |
| 794 | $CHF_2$ | H | H | Cl | Cl | $CH_2C\equiv CH$ | Ph | |
| 795 | $CHF_2$ | H | H | F | Cl | $CH_2$-cPr | Ph | |
| 796 | $CHF_2$ | H | H | F | Cl | $CH_2$-cPr | Ph-4-OMe | |
| 797 | $CHF_2$ | H | H | F | Cl | $CH_2$-cPr | Ph-2-F-5-Me | |
| 798 | $CHF_2$ | H | H | F | Cl | $CH_2CH_2Cl$ | Ph | |
| 799 | $CHF_2$ | H | H | F | Cl | $CH_2CH_3$ | Ph | |
| 800 | $CHF_2$ | H | H | F | Cl | $CH_2C\equiv CH$ | Ph | |
| 801 | $CHF_2$ | H | H | Cl | F | $CH_2$-cPr | Ph | |
| 802 | $CHF_2$ | H | H | Cl | F | $CH_2$-cPr | Ph-4-OMe | |
| 803 | $CHF_2$ | H | H | Cl | F | $CH_2$-cPr | Ph-2-F-5-Me | |
| 804 | $CHF_2$ | H | H | Cl | F | $CH_2CH_2Cl$ | Ph | |
| 805 | $CHF_2$ | H | H | Cl | F | $CH_2CH_3$ | Ph | |
| 806 | $CHF_2$ | H | H | Cl | F | $CH_2C\equiv CH$ | Ph | |
| 807 | $CF_3$ | H | H | H | F | $CH_2CF_3$ | Ph | |
| 808 | $CF_3$ | H | H | H | F | $CH_2Cl$ | Ph | |
| 809 | $CF_3$ | H | H | H | F | $CH_2CH_2Br$ | Ph | |
| 810 | $CF_3$ | H | H | H | F | $CH_2OEt$ | Ph | |
| 811 | $CF_3$ | H | H | H | F | $CH_2CH_2OME$ | Ph | |
| 812 | $CF_3$ | H | H | H | F | $CH_2cPent$ | Ph | |
| 813 | $CF_3$ | H | H | H | F | $CH_2cHex$ | Ph | |
| 814 | $CF_3$ | H | H | H | F | $CH_2cPr$-2,2-$Cl_2$ | Ph | |
| 815 | $CF_3$ | H | H | H | F | $CH_2cPr$-2,2-$Br_2$ | Ph | |
| 816 | $CF_3$ | H | H | H | F | $CH_2SMe$ | Ph | $n_D^{23.2}$ 1.5469 |
| 817 | $CF_3$ | H | H | H | F | $CH_2SOMe$ | Ph | $n_D^{26.0}$ 1.5462 |
| 818 | $CF_3$ | H | H | H | F | $CH_2SO_2Me$ | Ph | 116–117 |
| 819 | $CF_3$ | H | H | H | F | $CH_2CO_2Me$ | Ph | $n_D^{22.8}$ 1.5194 |
| 820 | $CF_3$ | H | H | H | F | $CH_2CO_2Et$ | Ph | $n_D^{22.8}$ 1.5167 |
| 821 | $CF_3$ | H | H | H | F | $CH_2CH_2CO_2Me$ | Ph | |
| 822 | $CF_3$ | H | H | H | F | $CH_2NMe_2$ | Ph | |
| 823 | $CF_3$ | H | H | H | F | $CH_2NHMe$ | Ph | |
| 824 | $CF_3$ | H | H | H | F | $CH_2CH_2NMe_2$ | Ph | |
| 825 | $CF_3$ | H | H | H | F | $CH_2CONH_2$ | Ph | $n_D^{24.5}$ 1.5380 |
| 826 | $CF_3$ | H | H | H | F | $CH_2CONHMe$ | Ph | |
| 827 | $CF_3$ | H | H | H | F | $CH_2CONMe_2$ | Ph | $n_D^{23.3}$ 1.5302 |
| 828 | $CF_3$ | H | H | H | F | $CH_2CH=CHCF_3$ | Ph | |
| 829 | $CF_3$ | H | H | H | F | $CH_2CH=CF_2$ | Ph | |
| 830 | $CF_3$ | H | H | H | F | $CH_2C(Br)=CH_2$ | Ph | |
| 831 | $CF_3$ | H | H | H | F | $CH_2C\equiv CCH_3$ | Ph | |
| 832 | $CF_3$ | H | H | H | F | $CH_2CH_2C\equiv CH$ | Ph | |
| 833 | $CF_3$ | H | H | H | F | $CH_2C\equiv CCF_3$ | Ph | |
| 834 | $CF_3$ | H | H | F | F | $CH_2CF_3$ | Ph | |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 835 | CF₃ | H | H | F | F | CH₂Cl | Ph | |
| 836 | CF₃ | H | H | F | F | CH₂CH₂Br | Ph | |
| 837 | CF₃ | H | H | F | F | CH₂OEt | Ph | |
| 838 | CF₃ | H | H | F | F | CH₂CH₂OMe | Ph | |
| 839 | CF₃ | H | H | F | F | CH₂cPent | Ph | |
| 840 | CF₃ | H | H | F | F | CH₂cHex | Ph | |
| 841 | CF₃ | H | H | F | F | CH₂-2,2-Cl₂-cPr | Ph | |
| 842 | CF₃ | H | H | F | F | CH₂-2,2-Br₂-cPr | Ph | |
| 843 | CF₃ | H | H | F | F | CH₂SMe | Ph | |
| 844 | CF₃ | H | H | F | F | CH₂SOMe | Ph | |
| 845 | CF₃ | H | H | F | F | CH₂SO₂Me | Ph | |
| 846 | CF₃ | H | H | F | F | CH₂CO₂Me | Ph | |
| 847 | CF₃ | H | H | F | F | CH₂CO₂Et | Ph | $n_D^{24.0}$ 1.5066 |
| 848 | CF₃ | H | H | F | F | CH₂CH₂CO₂Me | Ph | |
| 849 | CF₃ | H | H | F | F | CH₂NMe₂ | Ph | |
| 850 | CF₃ | H | H | F | F | CH₂NHMe | Ph | |
| 851 | CF₃ | H | H | F | F | CH₂CH₂NMe₂ | Ph | |
| 852 | CF₃ | H | H | F | F | CH₂CONH₂ | Ph | |
| 853 | CF₃ | H | H | F | F | CH₂CONHMe | Ph | |
| 854 | CF₃ | H | H | F | F | CH₂CONMe₂ | Ph | |
| 855 | CF₃ | H | H | F | F | CH₂CH=CHCF₃ | Ph | |
| 856 | CF₃ | H | H | F | F | CH₂CH=CF₂ | Ph | |
| 857 | CF₃ | H | H | F | F | CH₂C(Br)=CH₂ | Ph | |
| 858 | CF₃ | H | H | F | F | CH₂C≡CCH₃ | Ph | |
| 859 | CF₃ | H | H | F | F | CH₂CH₂C≡CH | Ph | |
| 860 | CF₃ | H | H | F | F | CH₂C≡CCF₃ | Ph | |
| 861 | CF₃ | H | H | H | F | CH₂cPr | Ph-2-Cl | 82–83 |
| 862 | CF₃ | H | H | H | F | CH₂cPr | Ph-4-Br | 89–90 |
| 863 | CF₃ | H | H | H | F | CH₂cPr | Ph-2-Cl-4-F | |
| 864 | CF₃ | H | H | H | F | CH₂cPr | Ph-2-Br-4-Me | |
| 865 | CF₃ | H | H | H | F | CH₂cPr | Ph-4-Et | |
| 866 | CF₃ | H | H | H | F | CH₂cPr | Ph-4-OEt | |
| 867 | CF₃ | H | H | H | F | CH₂cPr | Ph-4-OiPr | |
| 868 | CF₃ | H | H | H | F | CH₂cPr | Ph-4-OCH₂CH=CH₂ | 65–67 |
| 869 | CF₃ | H | H | H | F | CH₂cPr | Ph-4-OCH₂C≡CH | 77–78 |
| 870 | CF₃ | H | H | H | F | CH₂cPr | Ph-3-CF₃ | 77–78 |
| 871 | CF₃ | H | H | H | F | CH₂cPr | Ph-4-CF₃ | 124–125 |
| 872 | CF₃ | H | H | H | F | CH₂cPr | Ph-4-CF₂CF₂H | |
| 873 | CF₃ | H | H | H | F | CH₂cPr | Ph-4-OCF₃ | 96–97 |
| 874 | CF₃ | H | H | H | F | CH₂cPr | Ph-4-OCF₂H | |
| 875 | CF₃ | H | H | H | F | CH₂cPr | Ph-4-OCF₂CF₃ | |
| 876 | CF₃ | H | H | H | F | CH₂cPr | Ph-4-OCF₂CF₂H | |
| 877 | CF₃ | H | H | H | F | CH₂cPr | 1-Me-2-Pyrrolyl | |
| 878 | CF₃ | H | H | H | F | CH₂cPr | 1-Me-3-Pyrrolyl | |
| 879 | CF₃ | H | H | H | F | CH₂cPr | 2-Pyrrolyl | |
| 880 | CF₃ | H | H | H | F | CH₂cPr | 3-Pyrrolyl | |
| 881 | CF₃ | H | H | F | F | CH₂cPr | Ph-2-Cl | |
| 882 | CF₃ | H | H | F | F | CH₂cPr | Ph-4-Br | |
| 883 | CF₃ | H | H | F | F | CH₂cPr | Ph-2-Cl-4-F | |
| 884 | CF₃ | H | H | F | F | CH₂cPr | Ph-2-Br-4-CH₃ | |
| 885 | CF₃ | H | H | F | F | CH₂cPr | Ph-4-Et | |
| 886 | CF₃ | H | H | F | F | CH₂cPr | Ph-4-OEt | |
| 887 | CF₃ | H | H | F | F | CH₂cPr | Ph-4-OiPr | |
| 888 | CF₃ | H | H | F | F | CH₂cPr | Ph-4-OCH₂CH=CH₂ | |
| 889 | CF₃ | H | H | F | F | CH₂cPr | Ph-4-OCH₂C≡CH | |
| 890 | CF₃ | H | H | F | F | CH₂cPr | Ph-3-CF₃ | |
| 891 | CF₃ | H | H | F | F | CH₂cPr | Ph-4-CF₃ | |
| 892 | CF₃ | H | H | F | F | CH₂cPr | Ph-4-CF₂CF₂H | |
| 893 | CF₃ | H | H | F | F | CH₂cPr | Ph-4-OCF₃ | |
| 894 | CF₃ | H | H | F | F | CH₂cPr | Ph-4-OCF₂H | |
| 895 | CF₃ | H | H | F | F | CH₂cPr | Ph-4-OCF₂CF₃ | |
| 896 | CF₃ | H | H | F | F | CH₂cPr | Ph-4-OCF₂CF₂H | |
| 897 | CF₃ | H | H | F | F | CH₂cPr | 1-Me-2-Pyrrolyl | |
| 898 | CF₃ | H | H | F | F | CH₂cPr | 1-Me-3-Pyrrolyl | |
| 899 | CF₃ | H | H | F | F | CH₂cPr | 2-Pyrrolyl | |
| 900 | CF₃ | H | H | F | F | CH₂cPr | 3-Pyrrolyl | |

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|
| 901 | $CF_3$ | H | H | F | Br | $CH_2cPr$ | Ph | $n_D^{22.0}$ 1.5349 |
| 902 | $CF_3$ | H | H | H | Et | $CH_2cPr$ | Ph | |
| 903 | $CF_3$ | H | H | H | nPr | $CH_2cPr$ | Ph | |
| 904 | $CF_3$ | H | H | H | nBu | $CH_2cPr$ | Ph | |
| 905 | $CF_3$ | H | H | H | tBu | $CH_2cPr$ | Ph | |
| 906 | $CF_3$ | H | H | H | $C_2F_5$ | $CH_2cPr$ | Ph | |
| 907 | $CF_3$ | H | H | H | OEt | $CH_2cPr$ | Ph | |
| 908 | $CF_3$ | H | H | H | OnPr | $CH_2cPr$ | Ph | |
| 909 | $CF_3$ | H | H | H | OiPr | $CH_2cPr$ | Ph | |
| 910 | $CF_3$ | H | H | H | OtBu | $CH_2cPr$ | Ph | |
| 911 | $CF_3$ | H | H | OEt | F | $CH_2cPr$ | Ph | |
| 912 | $CF_3$ | H | H | OnPr | F | $CH_2cPr$ | Ph | |
| 913 | $CF_3$ | H | H | OiPr | F | $CH_2cPr$ | Ph | |
| 914 | $CF_3$ | H | H | OtBu | F | $CH_2cPr$ | Ph | |
| 915 | $CF_3$ | H | H | H | SOMe | $CH_2cPr$ | Ph | $n_D^{23.3}$ 1.5450 |
| 916 | $CF_3$ | H | H | H | $SO_2Me$ | $CH_2cPr$ | Ph | 144–146 |
| 917 | $CF_3$ | H | H | H | SEt | $CH_2cPr$ | Ph | |
| 918 | $CF_3$ | H | H | H | S-iPr | $CH_2cPr$ | Ph | |
| 919 | $CF_3$ | H | H | SOMe | F | $CH_2cPr$ | Ph | |
| 920 | $CF_3$ | H | H | $SO_2Me$ | F | $CH_2cPr$ | Ph | |
| 921 | $CF_3$ | H | H | SEt | F | $CH_2cPr$ | Ph | |
| 922 | $CF_3$ | H | H | S-iPr | F | $CH_2cPr$ | Ph | |
| 923 | $CF_3$ | H | H | $OCF_3$ | F | $CH_2cPr$ | Ph-4-OMe | |
| 924 | $CF_3$ | H | H | $OCF_3$ | F | $CH_2cPr$ | Ph-2-F | |
| 925 | $CF_3$ | H | H | $OCF_3$ | F | $CH_2cPr$ | Ph-4-F | |
| 926 | $CF_3$ | H | H | $OCF_3$ | F | $CH_2cPr$ | Ph | |
| 927 | $CF_3$ | H | H | $NO_2$ | $OCH_3$ | $CH_2cPr$ | Ph | |
| 928 | $CF_3$ | H | H | NHAc | F | $CH_2cPr$ | Ph | |
| 929 | $CF_3$ | H | H | $NH_2$ | F | $CH_2cPr$ | Ph | |
| 930 | $CF_3$ | H | H | F | F | $CH_2COOH$ | Ph | 113–120 |
| 931 | $CF_3$ | H | H | F | F | $CH_2cPr$ | 2-imidazolyl | |
| 932 | $CF_3$ | H | H | F | F | $CH_2cPr$ | 1-methyl-2-imidazolyl | |
| 933 | $CF_3$ | H | H | F | F | $CH_2cPr$ | 1-methyl-2-oxazolyl | |
| 934 | $CF_3$ | H | H | F | F | $CH_2cPr$ | 2-isoxazolyl | |
| 935 | $CF_3$ | H | H | F | F | $CH_2cPr$ | 1-methyl-2-isoxazolyl | |
| 936 | $CF_3$ | H | H | F | F | $CH_2cPr$ | 2-pyrimidinyl | |
| 937 | $CF_3$ | H | H | F | F | $CH_2cPr$ | 4,6-dimethyl-2-pyrimidinyl | |
| 938 | $CF_3$ | H | H | F | F | $CH_2cPr$ | 2-thiazolyl | |
| 939 | $CF_3$ | H | H | F | F | $CH_2cPr$ | 3-chloro-2-thiazolyl | |
| 940 | $CF_3$ | H | H | F | F | $CH_2cPr$ | 1-pyrazinyl | |
| 941 | $CF_3$ | H | H | F | F | $CH_2cPr$ | 3-mrthyl-1-pyrazinyl | |
| 942 | $CF_3$ | H | H | F | F | $CH_2cPr$ | 3-pyridazinyl | |
| 943 | $CF_3$ | H | H | F | F | $CH_2cPr$ | 3-methyl-4-pyridazinyl | |
| 944 | $CF_3$ | H | H | F | F | $CH_2cPr$ | 2-furyl | |
| 945 | $CF_3$ | H | H | F | F | $CH_2cPr$ | 3-bromo-2-furyl | |
| 946 | $CF_3$ | H | H | F | F | $CH_2cPr$ | 4-thiazolyl | |

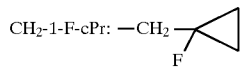

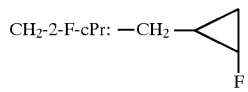

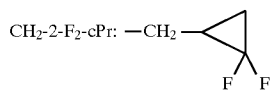

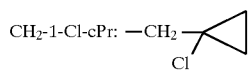

TABLE 3-continued (r¹, r² = H)

| No. | X¹ | X² | X³ | X⁴ | X⁵ | R¹ | R² | Physical const. mp. (°C.) refractive index |
|---|---|---|---|---|---|---|---|---|

CH₂-2-Cl-cPr: —CH₂—(cyclopropyl-Cl)

CH₂-2-Cl₂-cPr: —CH₂—(cyclopropyl-Cl,Cl)

CH₂-cPent: —CH₂—(cyclopentyl)

CH₂-1-Br-cPr: —CH₂—(cyclopropyl-1-Br)

CH₂-2-Br-cPr: —CH₂—(cyclopropyl-2-Br)

CH₂-2-Br₂-cPr: —CH₂—(cyclopropyl-Br,Br)

CH₂-cHex: —CH₂—(cyclohexyl)

CH₂-cHxe-3: —CH₂—(cyclohexenyl)

CH₂-cHex-3,4-Br₂: —CH₂—(cyclohexyl-3,4-Br₂)

TABLE 4

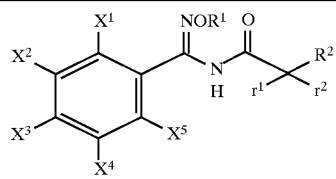

| No. | X¹ | X² | X³ | X⁴ | X⁵ | R¹ | r₁ | r₂ | R² | Physical const. mp. (°C.)/ refractive index |
|---|---|---|---|---|---|---|---|---|---|---|
| 947 | CF₃ | H | H | F | F | CH₂cPr | OMe | H | Ph | 25.4–1.5069 |
| 948 | CF₃ | H | H | F | F | CH₂cPr | Me | H | Ph | 25.5–1.5106 |
| 949 | CF₃ | H | H | F | F | CH₂cPr | Et | H | Ph | 25.4–1.5003 |
| 950 | CF₃ | H | H | F | F | CH₂cPr | OMe | CF₃ | Ph | 25.5–1.4855 |
| 951 | CF₃ | H | H | F | F | CH₂cPr | F | H | Ph | 25.5–1.5059 |
| 952 | CF₃ | H | H | F | F | CH₂cPr | Cl | H | Ph | 25.5–1.5244 |
| 953 | CF₃ | H | H | F | F | CH₂cPr | SMe | H | Ph | 25.5–1.5220 |
| 954 | CF₃ | H | H | F | F | CH₂cPr | =O | | Ph | 79–81 |
| 955 | CF₃ | H | H | F | F | CH₂cPr | Me | Me | Ph | 25.6–1.5105 |
| 956 | CF₃ | H | H | F | F | CH₂cPr | F | F | Ph | 50–52 |
| 957 | CF₃ | H | H | F | F | CH₂cPr | NHMe | H | Ph | |

TABLE 4-continued

| No. | $X^1$ | $X^2$ | $X^3$ | $X^4$ | $X^5$ | $R^1$ | $r_1$ | $r_2$ | $R^2$ | Physical const. mp. (°C.)/ refractive index |
|---|---|---|---|---|---|---|---|---|---|---|
| 958 | $CF_3$ | H | H | Cl | F | $CH_2cPr$ | OMe | H | Ph | |
| 959 | $CF_3$ | H | H | Cl | F | $CH_2cPr$ | Me | H | Ph | |
| 960 | $CF_3$ | H | H | Cl | F | $CH_2cPr$ | Et | H | Ph | |
| 961 | $CF_3$ | H | H | Cl | F | $CH_2cPr$ | OMe | $CF_3$ | Ph | |
| 962 | $CF_3$ | H | H | Cl | F | $CH_2cPr$ | F | H | Ph | |
| 963 | $CF_3$ | H | H | Cl | F | $CH_2cPr$ | Cl | H | Ph | |
| 964 | $CF_3$ | H | H | Cl | F | $CH_2cPr$ | SMe | H | Ph | |
| 965 | $CF_3$ | H | H | Cl | F | $CH_2cPr$ | =O | | Ph | |
| 966 | $CF_3$ | H | H | Cl | F | $CH_2cPr$ | Me | Me | Ph | |
| 967 | $CF_3$ | H | H | Cl | F | $CH_2cPr$ | F | F | Ph | |
| 968 | $CF_3$ | H | H | Cl | F | $CH_2cPr$ | NHMe | H | Ph | |
| 969 | $CF_3$ | H | H | F | Cl | $CH_2cPr$ | OMe | H | Ph | |
| 970 | $CF_3$ | H | H | F | Cl | $CH_2cPr$ | Me | H | Ph | |
| 971 | $CF_3$ | H | H | F | Cl | $CH_2cPr$ | Et | H | Ph | |
| 972 | $CF_3$ | H | H | F | Cl | $CH_2cPr$ | OMe | $CF_3$ | Ph | |
| 973 | $CF_3$ | H | H | F | Cl | $CH_2cPr$ | F | H | Ph | |
| 974 | $CF_3$ | H | H | F | Cl | $CH_2cPr$ | Cl | H | Ph | |
| 975 | $CF_3$ | H | H | F | Cl | $CH_2cPr$ | SMe | H | Ph | |
| 976 | $CF_3$ | H | H | F | Cl | $CH_2cPr$ | =O | | Ph | |
| 977 | $CF_3$ | H | H | F | Cl | $CH_2cPr$ | Me | Me | Ph | |
| 978 | $CF_3$ | H | H | F | Cl | $CH_2cPr$ | F | F | Ph | |
| 979 | $CF_3$ | H | H | F | Cl | $CH_2cPr$ | NHMe | H | Ph | |
| 980 | $CF_3$ | H | H | Cl | Cl | $CH_2cPr$ | OMe | H | Ph | |
| 981 | $CF_3$ | H | H | Cl | Cl | $CH_2cPr$ | Me | H | Ph | |
| 982 | $CF_3$ | H | H | Cl | Cl | $CH_2cPr$ | Et | H | Ph | |
| 983 | $CF_3$ | H | H | Cl | Cl | $CH_2cPr$ | OMe | $CF_3$ | Ph | |
| 984 | $CF_3$ | H | H | Cl | Cl | $CH_2cPr$ | F | H | Ph | |
| 985 | $CF_3$ | H | H | Cl | Cl | $CH_2cPr$ | Cl | H | Ph | |
| 986 | $CF_3$ | H | H | Cl | Cl | $CH_2cPr$ | SMe | H | Ph | |
| 987 | $CF_3$ | H | H | Cl | Cl | $CH_2cPr$ | =O | | Ph | |
| 988 | $CF_3$ | H | H | Cl | Cl | $CH_2cPr$ | Me | Me | Ph | |
| 989 | $CF_3$ | H | H | Cl | Cl | $CH_2cPr$ | F | F | Ph | |
| 990 | $CF_3$ | H | H | Cl | Cl | $CH_2cPr$ | NHMe | H | Ph | |
| 991 | $CF_3$ | H | H | H | F | $CH_2cPr$ | OMe | H | Ph | |
| 992 | $CF_3$ | H | H | H | F | $CH_2cPr$ | Me | H | Ph | |
| 993 | $CF_3$ | H | H | H | F | $CH_2cPr$ | Et | H | Ph | |
| 994 | $CF_3$ | H | H | H | F | $CH_2cPr$ | OMe | $CF_3$ | Ph | |
| 995 | $CF_3$ | H | H | H | F | $CH_2cPr$ | F | H | Ph | |
| 996 | $CF_3$ | H | H | H | F | $CH_2cPr$ | Cl | H | Ph | |
| 997 | $CF_3$ | H | H | H | F | $CH_2cPr$ | SMe | H | Ph | |
| 998 | $CF_3$ | H | H | H | F | $CH_2cPr$ | =O | | Ph | |
| 999 | $CF_3$ | H | H | H | F | $CH_2cPr$ | Me | Me | Ph | |
| 1000 | $CF_3$ | H | H | H | F | $CH_2cPr$ | F | F | Ph | |
| 1001 | $CF_3$ | H | H | H | F | $CH_2cPr$ | NHMe | H | Ph | |
| 1002 | $CF_3$ | H | H | F | F | Et | Me | H | Ph | |
| 1003 | $CF_3$ | H | H | F | F | $CH_2C\equiv CH$ | Me | H | Ph | |
| 1004 | $CF_3$ | H | H | F | F | $CH_2CH_2Cl$ | Me | H | Ph | |
| 1005 | $CF_3$ | H | H | F | F | Et | Me | H | Ph-4-OMe | |
| 1006 | $CF_3$ | H | H | F | F | $CH_2C\equiv CH$ | Me | H | Ph-4-OMe | |
| 1007 | $CF_3$ | H | H | F | F | $CH_2CH_2Cl$ | Me | H | Ph-4-OMe | |
| 1008 | $CF_3$ | H | H | F | Cl | Et | Me | H | Ph | |
| 1009 | $CF_3$ | H | H | F | Cl | $CH_2C\equiv CH$ | Me | H | Ph | |
| 1010 | $CF_3$ | H | H | F | Cl | $CH_2CH_2Cl$ | Me | H | Ph | |
| 1011 | $CF_3$ | H | H | F | Cl | Et | Me | H | Ph-4-OMe | |
| 1012 | $CF_3$ | H | H | F | Cl | $CH_2C\equiv CH$ | Me | H | Ph-4-OMe | |
| 1013 | $CF_3$ | H | H | F | Cl | $CH_2CH_2Cl$ | Me | H | Ph-4-OMe | |
| 1014 | $CF_3$ | H | H | Cl | F | Et | Me | H | Ph | |
| 1015 | $CF_3$ | H | H | Cl | F | $CH_2C\equiv CH$ | Me | H | Ph | |
| 1016 | $CF_3$ | H | H | Cl | F | $CH_2CH_2Cl$ | Me | H | Ph | |
| 1017 | $CF_3$ | H | H | Cl | F | Et | Me | H | Ph-4-OMe | |
| 1018 | $CF_3$ | H | H | Cl | F | $CH_2C\equiv CH$ | Me | H | Ph-4-OMe | |

TABLE 4-continued

Structure: X1, X2, X3, X4, X5 on benzene ring with C(=NOR1)-NH-C(=O)-CR2(r1)(r2) side chain

| No. | X¹ | X² | X³ | X⁴ | X⁵ | R¹ | r₁ | r₂ | R² | Physical const. mp. (°C.)/ refractive index |
|---|---|---|---|---|---|---|---|---|---|---|
| 1019 | CF₃ | H | H | Cl | F | CH₂CH₂Cl | Me | H | Ph-4-OMe | |
| 1020 | CF₃ | H | H | Cl | Cl | Et | Me | H | Ph | |
| 1021 | CF₃ | H | H | Cl | Cl | CH₂C≡CH | Me | H | Ph | |
| 1022 | CF₃ | H | H | Cl | Cl | CH₂CH₂Cl | Me | H | Ph | |
| 1023 | CF₃ | H | H | Cl | Cl | Et | Me | H | Ph-4-OMe | |
| 1024 | CF₃ | H | H | Cl | Cl | CH₂C≡CH | Me | H | Ph-4-OMe | |
| 1025 | CF₃ | H | H | Cl | Cl | CH₂CH₂Cl | Me | H | Ph-4-OMe | |
| 1026 | CF₃ | H | H | H | F | Et | Me | H | Ph | |
| 1027 | CF₃ | H | H | H | F | CH₂C≡CH | Me | H | Ph | |
| 1028 | CF₃ | H | H | H | F | CH₂CH₂Cl | Me | H | Ph | |
| 1029 | CF₃ | H | H | H | F | Et | Me | H | Ph-4-OMe | |
| 1030 | CF₃ | H | H | H | F | CH₂C≡CH | Me | H | Ph-4-OMe | |
| 1031 | CF₃ | H | H | H | F | CH₂CH₂Cl | Me | H | Ph-4-OMe | |
| 1032 | CF₃ | H | H | F | F | CH₂CN | H | H | Ph | 77–80 |
| 1033 | CF₃ | H | H | F | Cl | CH₂CN | H | H | Ph | |
| 1034 | CF₃ | H | H | F | F | CH₂CH(OEt)₂ | H | H | Ph | |
| 1035 | CF₃ | H | H | F | Cl | CH₂CH(OEt)₂ | H | H | Ph | |
| 1036 | CF₃ | H | H | NO₂ | OEt | CH₂cPr | H | H | Ph | 62–63 |

*25.4–1.5069 means $n_D^{25.4}$ 1.5069 (refractive index) in the above tables.

¹H-NMR data (CDCl₃, δ ppm from TMS); *1 Compound No. 346; 0.1~0.2 (2H, m), 0.45~0.55 (2H, m), 0.95~1.1 (1H, m), 3.60 (2H, s), 3.8~3.9 (2H, m), 3.82 (3H, s), 6.92 (2H, d), 7.1~7.25 (3H, m), 7.51 (1H, dd), 8.53 (1H, brs)

The compounds of the present invention can show excellent fungicidal activity against wide varieties of fungi, and therefore, the compounds can be useful for plant disease control in the farming of agricultural and horticultural crops including ornamental flowers, turf and forage crops.

The examples for the plant diseases to be controlled with the compounds of the present invention are given in the following.

| | | |
|---|---|---|
| Paddy rice | Blast | (Pyricularia oryzae) |
| | Sheath blight | (Rhizoctonia solani) |
| | Bakanae disease | (Gibberella fujikuroi) |
| | Helminthosporium leaf spot | (Cochliobolus miyabeanus) |
| Barley | Loose smut | (Ustilago nuda) |
| Wheat | Scab | (Gibberella zeae) |
| | Leaf rust | (Puccinia recondita) |
| | Eye spot | (Pseudocercosporella herpotrichoides) |
| | Glume blotch | (Leptosphaeria nodorum) |
| | Powdery mildew | (Erysiphe graminis f. sp. tritici) |
| | Fusarium snow blight | (Micronectriella nivalis) |
| Potato | Late blight | (Phytophthora infestans) |
| Ground nut | Leaf spot | (Mycosphaerella aradius) |
| Sugar beat | Cercospora leaf spot | (Cercospora beticola) |
| Cucumber | Powdery mildew | (Sphaerotheca fuliginea) |
| | Sclerotinia rot | (Sclerotinia sclerotiorum) |
| | Gray mold | (Botrytis cinerea) |
| | Downy mildew | (Pseudoperonospora cubensis) |
| Tomato | Leaf mold | (Cladosporium fulvum) |
| | Late blight | (Phytophthora infestans) |
| Egg plant | Black rot | (Corynespora melongenae) |
| Onion | Gray-mold neck rot | (Botrytis allii) |
| Strawberry | Powdery mildew | (Sphaerotheca humuli) |
| Apple | Powdery mildew | (Podosphaera leucotricha) |
| | Scab | (Venturia inaequalis) |
| | Blossom blight | (Monilinia mali) |
| Persimmon | Anthracnose | (Gloeosporium kaki) |
| Peach | Brown rot | (Monilinia fructicola) |
| Grape | Powdery mildew | (Uncinula necator) |
| | Downy mildew | (Plasmopara viticola) |
| Pear | Rust | (Gymnosporangium asiaticum) |
| | Black spot | (Alternaria kikuchiana) |
| Tea-plant | Leaf spot | (Pestalotia theae) |
| | Anthracnose | (Colletotrichum theae-sinensis) |
| Orange | Scab | (Elsinoe fawcetti) |
| | Blue mold | (Penicillium italicum) |
| Turf | Sclerotinia snow blight | (Sclerotinia borealis) |

In recent years, it is known that various pathogenic fungi have developed their resistance to benzimidazole fungicides and ergosterol biosynthesis inhibitors and that such fungicides have been insufficient in their fungicidal effectiveness. Therefore, it is required to provide new compounds useful as a fungicide which are effective to the resistant-strain of such pathogenic fungi as well. The compounds of the present invention are the ones which can be a fungicide having excellent fungicidal effectiveness not only to the susceptible-strains of pathogenic fungi but also to the resistant-strains of pathogenic fungi to benzimidazole fungicides and ergosterol biosynthesis inhibitors.

For the preferable examples of plant diseases to be applied with the compounds of the present invention, powdery mildew on wheat, powdery mildew on cucumber, powdery mildew on strawberries, etc. can be given.

The compounds of the present invention can be utilized as an antifouling agent for preventing the adhesion of aqueous organisms to structures, such as the bottom of a ship and fishing nets, in water and sea.

Also, the compounds of the present invention can be contained in paints and fibers and thereby used as an antimicrobial agent for walls, bathtubs, shoes and clothes.

Furthermore, some of the compounds of the present invention can show insecticidal, acaricidal and herbicidal activities.

In the practical application of the compounds of the present invention obtained as described above, the compounds can be used in the state as it is without formulation, or, for the use as agricultural plant protection chemicals, the compounds can be applied in forms of general formulations for agricultural plant protection chemicals, such as wettable powders, granules, powders, emulsifiable concentrates, aqueous solutions, suspensions and flowables. For the additives and carriers to be used in the formulations described above, vegetable powders, such as soybean powder and wheat powder, mineral fine powders, such as diatomaceous earth, apatite, gypsum, talc, bentonite, pyrophyllite and clay, and organic and inorganic compounds, such as sodium benzoate, urea and Glauber's salt, can be used, when the compounds are formulated into solid formulations. Whereas, when the compounds are formulated into liquid formulations, petroleum fractions, such as kerosine, xylene and solvent naphtha, cyclohexane, cyclohexanone, dimethyl formamide, dimethyl sulfoxide, alcohols, acetone, trichloro ethylene, methylisobutyl ketone, mineral oils, vegetable oils and water, can be used as the solvent. In these formulations, surface active agents may be added to the formulations in order to make the formulations homogeneous and stable, if appropriate.

The content of the compound of the present invention as the active principle in the formulations is preferably in a range of from 5 to 70%.

The wettable powders, the emulsifiable concentrates and the flowable formulation comprising the compound of the present invention prepared as described above can be applied in a form prepared by diluting the formulations with water to the suspension or the emulsion at a desired concentrations, while the powders and the granules of the said compound can be directly applied to plants without dilution.

The compounds of the present invention can demonstrate sufficient effectiveness on plant diseases independently, however, it is also possible to use the said compound in admixing with 1 or more of other fungicides, insecticides, acaricides or synergists.

The followings are the examples for the fungicides, insecticides, acaricides, nematocides and plant growth regulators, those which are usable in admixing with the compounds of the present invention.

Fungicides:
Copper-based fungicides:
  Basic copper chloride, basic copper sulfate, etc.
Sulphur-based fungicides:
  Thiram, maneb, mancozeb, polycarbamate, propineb, ziram, zineb, etc.
Polyhaloalkylthio fungicides:
  Captan, dichlofluanid, folpet, etc.
Organochlorine fungicides:
  Chlorothalonil, fthalide, etc.
Organophosphorous fungicides:
  IBP, EDDP, tolclofos-methyl, pyrazophos, fosetyl-Al, etc.
Benzimidazole fungicides:
  Thiophanate-methyl, benomyl, carbendazim, thiabendazole, etc.
Dicarboxyimide fungicides:
  Oxycarboxine, mepronyl, flutolanil, techlofthalam, trichlamide, pencycuron, etc.
Acyl alanine fungicides:
  Metalaxyl, oxadixyl, furalaxyl etc.
EBI fungicides:
  Triadimefon, triadomenol, bitertanol, microbutanil, hexaconazol, propiconazole, triflumizole, procloraz, peflazoate, fenarimol, pyrifenox, trifolin, flusilazole, etaconazole, diclobutrazol, fluotrimazole, flutriafen, penconazole, diniconazole, cyproconazole, imazalil, tridemorph, fenpropimorph, buthiobate, etc.
Antibiotics:
  Polyoxin, blasticidin-S, kasugamycin, validamycin, streptomycin sulfate, etc.
Others:
  Propamocarb hydrochloride salt, quintozene, hydroxyisoxazole, metasulfocarb, anilazine, isoprothiolane, probenazole, quinomethionate, dithianone, dinocap, dichlomezine, mepaniprim, ferimzone, fluazinam, pyroquilon, tricyclazole, oxolinic acid, dithianone, iminoctazine acetate salt, cymoxanil, pyrrolenitrine, metasulfocarb, diethofencarb, binapacryl, lecithin, sodium hydrogencarbonate, fenaminosulf, dodine, dimethomorph, fenazine oxide, etc.
Insecticides and Acaricides:
Organophosphorous and carbamate insecticides:
  Fenthion, fenitrothion, diazinon, chlorpyrifos, ESP, vamidothion, fenthoate, dimethoate, formothion, malathon, trichlorfon, thiometon, phosmet, dichlorvos, acephate, EPBP, methyl parathion, oxydimeton methyl, ethion, salithion, cyanophos, isoxathion, pyridafenthion, phosalon, methydathion, sulprofos, chlorfenvinphos, tetrachlorvinphos, dimethylvinphos, propaphos, isofenphos, ethylthiometon, profenofos, pyraclophos, monocrotophos, azinphos methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb, cartap, thiocyclam, bensultap, etc.
Pyrethroid insecticides:
  Permethrin, cypermethrin, deltamethrin, fenvalerate, fenpropathrin, pyrethrin, allethrin, tetramethrin, resmethrin, dimethrin, propathrin, fenothrin, prothrin, fluvalinate, cyfluthrin, cyhalothrin, flucythrinate, ethofenprox, cycloprothrin, tralomethrin, silafluophen, brofenprox, acrinathrin, etc.
Benzoyl urea-based insecticides and others:
  Diflubenzuron, chlorfluazuron, hexaflumuron, triflumuron, tetrabenzuron, flufenoxuron, flucycloxuron, buprofezin, pyriproxyfen, methoprene, benzoepin, diaphenthiuron, imidacloprid, fipronil, nicotine sulfate, rotenone, meta-aldehyde, machine oil, *Bacillus thuringiensis*, microbial insecticides such as insect-pathogenic viruses, etc.
Nematocides:
  Fenamiphos, phosthiazate, etc.
Acaricides:
  Chlorbenzilate, phenisobromolate, dicofol, amitraz, BPPS, benzomate, hexythiazox, fenbutatin oxide, polynactin, quinomethionate, CPCBS, tetradifon, avermectin, milbemectin, chlofentezin, cyhexatin, pyridaben, fenpyroxymate, tebufenpyrad, pyrimidifen, fenothiocarb, dienochlor, etc.

Plant Growth Regulators:

Gibberellines (Gibberelline $A_3$, Gibberelline $A_4$, Gibberelline $A_7$, etc.), IAA, and NAA.

Now, the examples of the formulations comprising the compound of the present invention are described hereinbelow, however, it should be noted that the type and the rate of the additives shall not be limited to the ones described in the examples and can be replaced by wide range of other additives and/or carriers. In the examples hereinbelow, a part mentioned in each of the formulation examples represents a part by weight.

EXAMPLE 3

Wettable Powder

The compound of the present invention 40 parts

Diatomaceous earth 53 parts

Sulfuric acid ester of higher alcohol 4 parts

Alkyl naphthalene sulfonate 3 parts

All components are admixed and micronized to fine powder, thereby affording the wettable powder formulation containing the active principle at a concentration of 40%.

EXAMPLE 4

Emulsifiable Concentrate

The compound of the present invention 30 parts

Xylene 33 parts

Dimethyl formamide 30 parts

Polyoxy ethlene alkylally ether 7 parts

All components are admixed and then dissolved into a solution, thereby affording the emulsifiable concentrate formulation containing the active principle at a concentration of 30%.

EXAMPLE 5

Dust Formulation

The compound of the present invention 10 parts

Talc 89 parts

Polyoxy ethlene alkylally ether 1 parts

All components are admixed and pulverized to fine dusting powder, thereby affording the dust formulation containing the active principle at a concentration of 10%.

EXAMPLE 6

Granular Formulation

The compound of the present invention 5 parts

Clay 73 parts

Bentonite 20 parts

Sodium salt of dioctylsulfosuccinate 1 part

Sodium phosphate 1 part

All components are admixed, pulverized and then kneaded thoroughly while adding water, and then further granulated and dried, thereby affording the granular formulation containing the active principle at a concentration of 5%.

EXAMPLE 7

Suspension

The compound of the present invention 10 parts

Sodium lignin sulfonate 4 parts

Sodium dodecyl benzene sulfonate 1 part

Xanthane Gum 0.2 part

Water 84.8 parts

All components are admixed and subjected to wet grinding up to the particle size of less than $1\mu$, thereby affording the suspension containing the active principle at a concentration of 10%.

Now, the usefulness of the compounds of the present invention as the active principle of a plant protection chemical for controlling various plant diseases is shown in Test Examples described hereinbelow. The effectiveness of the compounds on plant disease control were assessed basing on the pathological changes in the state of plants provided, namely the degree of disease-induced lesion on leaves, stems and other parts of the plants was visually observed, respectively. The assessment was conducted by giving scores in effectiveness on plant diseases to each test plots as the following.

Score, 5; If no lesion were observed.

Score, 4; If the degree of the lesion observed were approximately 10% of the degree in the untreated plot.

Score, 3; If the degree of the lesion observed were approximately 25% of the degree in the untreated plot.

Score, 2; If the degree of the lesion observed were approximately 50% of the degree in the untreated plot.

Score, 1; If the degree of the lesion observed were approximately 75% of the degree in the untreated plot.

Score, 0; If the degree of the lesion observed were almost same as the degree in the untreated plot.

Test Example 1: Preventive Control Efficacy Test on Wheat Powdery Mildew

To young seedlings of wheat (Variety: Chihoku) grown in an unglazed pot, the emulsion at a concentration of 12.5 ppm prepared from the emulsifiable concentrate comprising the compound of the present invention were sprayed throughly. After the spraying, the seedlings were dried under natural condition and then inoculated by means of sprinkling with the conidia of the fungus causing wheat powdery mildew (*Erysiphe graminia* f. sp. *tritici*) and placed in a greenhouse maintained at around 20° C. for 7 days in order to complete the infection. Appearance of the lesion on leaves cause by the disease was assessed and compared with the lesion on leaves in the untreated plot, thereby evaluating the preventive efficacy of the compound to the disease. The results are shown in Table 5.

Test Example 2: Preventive Control Efficacy Test on Cucumber Powdery Mildew

To young seedlings of cucumber (Variety: Sagami-Hanjiro) grown in an unglazed pot, the emulsion at a concentration of 12.5 ppm prepared from the emulsifiable concentrate comprising the compound of the present invention were sprayed. After the spraying, the seedlings were dried under natural condition and then inoculated by means of sprinkling with the conidia of the fungus causing cucumber powdery mildew (*Sphaerotheca fuliginea*) and placed in a temperature-controlled room maintained at around 25° C. for 11 days in order to complete the infection. Appearance of powdery mildew-causing lesion on the leaves whereto the compound was sprayed was assessed and compared with the lesion appeared on leaves in the untreated plot, thereby evaluating the preventive efficacy of the compound to the disease. The results are shown in Table 5.

As shown in Table 5, it is demonstrated that the compounds of the present invention can show superior preventive control efficacy to not only wheat powdery mildew but also cucumber powdery mildew in comparison with other compounds tested.

Test Example 3: Test on Cucumber Powdery Mildew Control with Vapour

10 μl of the emulsion at a concentration of 500 ppm prepared from the emulsifiable concentrate comprising the compound of the present invention were fed dropwise onto round aluminium foils each having a diameter of 1 cm and dried at room temperature under natural condition.

The aluminium foils were then fixed on the upper side of the leaves of cucumber seedlings (Variety: Sagami-Hanjiro) grown in an unglazed pot. After 24 hours, the cucumber leaves were inoculated by means of sprinkling with the conidia of the fungus causing cucumber powdery mildew (*Sphaerotheca fuliginea*) and placed in a temperature-controlled room maintained at around 25° C. for 11 days in order to complete the infection. Appearance of powdery mildew-causing lesion on the leaves placed with the aluminium foil was assessed and compared with the lesion appeared on the leaves in the untreated plot. The control efficacy with the vapour of the compound to the disease was confirmed in case that disease lesion-free circle having a diameter of more than 2 cm is formed around the aluminium foil fixed on a leaf. The results are shown in Table 5.

On the other hand, other compounds for the comparison, which are disclosed in Japanese Patent Laid-opened No. Hei 2-6453 (see Table 5), did not show the control efficacy with the vapour to the disease.

Since the compounds of the present invention have vapour action, it is suggested that the compound of the present invention can show plant disease control efficacy even in the inner space of leaves and fruits of crops whereto spraying of a fungicide in even condition is generally rather difficult.

TABLE 5

| No. | Concentration of active ingredient (ppm) | Wheat Powdery mildew | Cucumber Powdery mildew | Vapar action |
|---|---|---|---|---|
| 1 | 12.5 | 5 | 5 | |
| 3 | 12.5 | 5 | 5 | |
| 4 | 12.5 | 5 | 5 | |
| 5 | 12.5 | 5 | 5 | |
| 6 | 12.5 | 5 | 5 | |
| 7 | 12.5 | 4 | 5 | |
| 8 | 12.5 | 5 | 5 | |
| 9 | 12.5 | 5 | 5 | |
| 10 | 12.5 | 4 | 5 | |
| 11 | 12.5 | 5 | 5 | |
| 12 | 12.5 | 5 | 5 | |
| 13 | 12.5 | 5 | 5 | |
| 18 | 12.5 | 2 | 4 | |
| 19 | 12.5 | 4 | 5 | |
| 20 | 12.5 | 4 | 5 | |
| 22 | 12.5 | 5 | 5 | |
| 24 | 12.5 | 5 | 5 | good |
| 25 | 12.5 | 5 | 5 | |
| 27 | 12.5 | 5 | 5 | |
| 28 | 12.5 | 4 | 4 | |
| 29 | 12.5 | 4 | 4 | |
| 30 | 12.5 | 5 | 4 | |
| 32 | 12.5 | 4 | 4 | |
| 33 | 12.5 | 3 | 5 | |
| 34 | 12.5 | 4 | 5 | good |
| 35 | 12.5 | 5 | 5 | good |
| 36 | 12.5 | 5 | 4 | |
| 37 | 12.5 | 4 | 5 | good |
| 38 | 12.5 | 5 | 4 | |
| 39 | 12.5 | 5 | 5 | good |
| 42 | 12.5 | 5 | 5 | good |
| 43 | 12.5 | 5 | 5 | good |
| 44 | 12.5 | 5 | 5 | good |
| 45 | 12.5 | 4 | 4 | |
| 46 | 12.5 | 5 | 5 | |
| 47 | 12.5 | 5 | 5 | good |
| 48 | 12.5 | 5 | 5 | good |
| 49 | 12.5 | 5 | 5 | |
| 50 | 12.5 | 5 | 5 | good |
| 51 | 12.5 | 5 | 5 | good |
| 52 | 12.5 | 5 | 5 | good |
| 53 | 12.5 | 5 | 5 | |
| 54 | 12.5 | 5 | 5 | good |
| 55 | 12.5 | 5 | 5 | |
| 56 | 12.5 | 5 | 5 | good |
| 57 | 12.5 | 5 | 5 | good |
| 58 | 12.5 | 4 | 4 | |
| 59 | 12.5 | 4 | 4 | |
| 60 | 12.5 | 4 | 5 | |
| 62 | 12.5 | 4 | 5 | |
| 64 | 12.5 | 4 | 4 | |
| 65 | 12.5 | 5 | 5 | |
| 66 | 12.5 | 5 | 5 | |
| 68 | 12.5 | 5 | 5 | |
| 71 | 12.5 | 5 | 4 | |
| 74 | 12.5 | 5 | 5 | |
| 82 | 12.5 | 5 | 5 | |
| 96 | 12.5 | 5 | 5 | good |
| 99 | 12.5 | 5 | 5 | good |
| 105 | 12.5 | 5 | 5 | good |
| 112 | 12.5 | 5 | 5 | good |
| 113 | 12.5 | 5 | 5 | good |
| 114 | 12.5 | 4 | 5 | |
| 115 | 12.5 | 4 | 5 | |
| 140 | 12.5 | 3 | 5 | good |
| 149 | 12.5 | 5 | 5 | good |
| 156 | 12.5 | 5 | 5 | good |
| 157 | 12.5 | 5 | 5 | good |
| 209 | 12.5 | 4 | 4 | |
| 211 | 12.5 | 4 | 4 | |
| 212 | 12.5 | 5 | 5 | |
| 234 | 12.5 | 5 | 5 | good |
| 239 | 12.5 | 5 | 5 | good |
| 240 | 12.5 | 5 | 5 | good |
| 241 | 12.5 | 5 | 5 | good |
| 242 | 12.5 | 5 | 5 | good |
| 255 | 12.5 | 5 | 5 | good |
| 258 | 12.5 | 5 | 5 | good |
| 260 | 12.5 | 5 | 5 | good |
| 262 | 12.5 | 5 | 5 | good |
| 263 | 12.5 | 5 | 5 | |
| 264 | 12.5 | 5 | 5 | good |
| 266 | 12.5 | 5 | 5 | |
| 267 | 12.5 | 5 | 5 | good |
| 268 | 12.5 | 5 | 5 | |
| 269 | 12.5 | 5 | 5 | good |
| 270 | 12.5 | 5 | 5 | good |
| 271 | 12.5 | 5 | 5 | |
| 272 | 12.5 | 5 | 5 | good |
| 273 | 12.5 | 5 | 5 | good |
| 274 | 12.5 | 5 | 5 | |
| 275 | 12.5 | 5 | 5 | |
| 276 | 12.5 | 5 | 4 | |
| 277 | 12.5 | 5 | 5 | |
| 279 | 12.5 | 5 | 5 | good |
| 280 | 12.5 | 5 | 5 | |
| 286 | 12.5 | 5 | 5 | |
| 287 | 12.5 | 5 | 5 | |
| 288 | 12.5 | 5 | 5 | |
| 289 | 12.5 | 5 | 5 | |
| 290 | 12.5 | 5 | 5 | good |
| 293 | 12.5 | 4 | 5 | |
| 304 | 12.5 | 5 | 5 | |
| 307 | 12.5 | 5 | 5 | |
| 309 | 12.5 | 5 | 5 | good |
| 311 | 12.5 | 5 | 5 | good |
| 312 | 12.5 | 5 | 5 | |
| 313 | 12.5 | 5 | 5 | good |

TABLE 5-continued

| No. | Concentration of active ingredient (ppm) | Wheat Powdery mildew | Cucumber Powdery mildew | Vapar action |
|---|---|---|---|---|
| 315 | 12.5 | 5 | 5 | |
| 316 | 12.5 | 5 | 5 | |
| 319 | 12.5 | 5 | 5 | good |
| 320 | 12.5 | 5 | 5 | |
| 321 | 12.5 | 5 | 5 | |
| 322 | 12.5 | 5 | 5 | |
| 323 | 12.5 | 5 | 5 | |
| 324 | 12.5 | 4 | 4 | |
| 326 | 12.5 | 5 | 5 | |
| 328 | 12.5 | 5 | 5 | good |
| 333 | 12.5 | 5 | 5 | good |
| 346 | 12.5 | 5 | 4 | |
| 347 | 12.5 | 4 | 4 | |
| 348 | 12.5 | 3 | 4 | |
| 349 | 12.5 | 4 | 5 | |
| 351 | 12.5 | 5 | 4 | good |
| 352 | 12.5 | 5 | 4 | good |
| 353 | 12.5 | 5 | 4 | good |
| 364 | 12.5 | 5 | 5 | good |
| 367 | 12.5 | 5 | 5 | good |
| 368 | 12.5 | 5 | 5 | good |
| 370 | 12.5 | 5 | 5 | good |
| 371 | 12.5 | 5 | 5 | good |
| 372 | 12.5 | 5 | 5 | good |
| 373 | 12.5 | 5 | 5 | good |
| 374 | 12.5 | 5 | 5 | good |
| 375 | 12.5 | 5 | 5 | good |
| 376 | 12.5 | 5 | 5 | good |
| 377 | 12.5 | 5 | 5 | good |
| 378 | 12.5 | 5 | 5 | |
| 379 | 12.5 | 5 | 5 | good |
| 381 | 12.5 | 5 | 5 | good |
| 383 | 12.5 | 5 | 5 | good |
| 386 | 12.5 | 5 | 5 | good |
| 389 | 12.5 | 5 | 5 | good |
| 391 | 12.5 | 5 | 5 | |
| 392 | 12.5 | 5 | 5 | good |
| 393 | 12.5 | 5 | 5 | good |
| 395 | 12.5 | 5 | 5 | good |
| 396 | 12.5 | 5 | 5 | good |
| 399 | 12.5 | 4 | 5 | |
| 400 | 12.5 | 5 | 5 | |
| 401 | 12.5 | 5 | 5 | good |
| 402 | 12.5 | 5 | 5 | good |
| 403 | 12.5 | 5 | 5 | good |
| 404 | 12.5 | 5 | 5 | good |
| 405 | 12.5 | 5 | 5 | good |
| 406 | 12.5 | 5 | 5 | good |
| 407 | 12.5 | 5 | 5 | good |
| 408 | 12.5 | 5 | 5 | good |
| 409 | 12.5 | 5 | 5 | |
| 410 | 12.5 | 5 | 5 | |
| 413 | 12.5 | 5 | 5 | good |
| 414 | 12.5 | 5 | 5 | good |
| 415 | 12.5 | 5 | 5 | good |
| 429 | 12.5 | 5 | | |
| 430 | 12.5 | 5 | | |
| 442 | 12.5 | 5 | 5 | good |
| 445 | 12.5 | 5 | 5 | good |
| 447 | 12.5 | 5 | 5 | good |
| 451 | 12.5 | 5 | 5 | good |
| 453 | 12.5 | 5 | 5 | good |
| 454 | 12.5 | 5 | 5 | good |
| 455 | 12.5 | 5 | 5 | good |
| 456 | 12.5 | 5 | 5 | good |
| 457 | 12.5 | 5 | 5 | good |
| 458 | 12.5 | 5 | 5 | good |
| 459 | 12.5 | 5 | 5 | good |
| 508 | 12.5 | 5 | 5 | |
| 694 | 12.5 | 5 | | |
| 861 | 12.5 | 4 | | |
| 868 | 12.5 | 4 | | |
| 937 | 12.5 | 4 | | |

TABLE 5-continued

| No. | Concentration of active ingredient (ppm) | Wheat Powdery mildew | Cucumber Powdery mildew | Vapar action |
|---|---|---|---|---|
| Reference: | | | | |

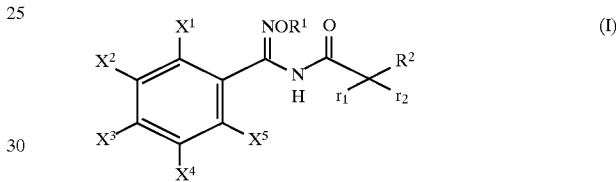

| | 12.5 | 5 | 1 | |

Industrial Applicability

The compounds of the present invention have excellent fungicidal effectiveness, and therefore, are useful as a fungicide for agricultural and horticultural use.

What is claimed is:

1. Benzamidoxime derivatives represented by the formula [I]:

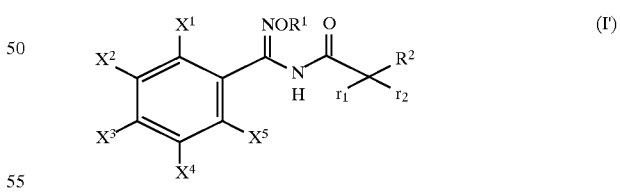

wherein $R^1$ is unsubstituted or substituted $C_1$–$C_4$ alkyl, unsubstituted or substituted $C_2$–$C_4$ alkenyl or unsubstituted or substituted $C_2$–$C_4$ alkynyl, $R^2$ is phenyl optionally having substituents, $X^1$ is $C_1$–$C_4$ haloalkyl, $X^2$, $X^3$, $X^4$ and $X^5$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, and $r_1$ and $r_2$ are each independently hydrogen, halogen, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may form carbonyl in together.

2. Benzamidoxime derivatives represented by the formula [I']:

$$\begin{array}{c}X^1\quad NOR^1\quad O\\X^2\diagdown\diagup C\diagdown N\diagdown C\diagup R^2\\|\quad|\\H\quad r_1\quad r_2\\X^3\diagdown\diagup X^5\\X^4\end{array}\quad (I')$$

wherein $R^1$ is straight-chain or branched $C_1$–$C_4$ alkyl; a group represented by a general formula, $R^3CH_2$, wherein $R^3$ is a group selected from a group consisting of $C_3$–$C_8$ cycloalkyl, $C_1$–$C_3$ haloalkyl, $C_1$–$C_3$ alkoxy, $C_1$–$C_3$ alkylthio, $C_1$–$C_3$ alkylsulfinyl, $C_1$–$C_3$ alkylsulfonyl, $C_1$–$C_3$ alkoxycarbonyl, cyano, amino, $C_1$–$C_3$ monoalkylamino, $C_1$–$C_3$ dialkylamino, acylamino and cyano; $C_2$–$C_4$ alkenyl or $C_2$–$C_4$ alkynyl, $R^2$ is phenyl optionally having one or more substituents selected from a group consisting of halogen, $C_1$–$C_3$ alkyl, $C_1$–$C_3$ alkoxy, $C_1$–$C_3$ haloalkyl and $C_1$–$C_3$ haloalkoxy;

$X^1$ is $C_1$–$C_4$ haloalkyl, $X^2$, $X^3$, $X^4$ and $X^5$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, and $r_1$ and $r_2$ are each independently hydrogen, halogen, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may form carbonyl in together.

3. A fungicide for argricultural and horticultural use, comprising one or more of the benzamidoxime derivatives represented by the formula (I) in claim 1 wherein $R^1$, $X^1$, $X^2$, $X^3$, $X^4$, $X^5$, $R^2$, $r_1$ and $r_2$ are as defined in claim 1 as the active principle and a carrier.

4. Benzamidoxime derivatives represented by the formula (I'):

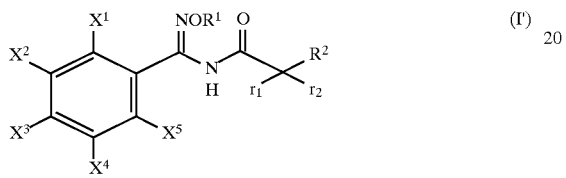

wherein $R^1$ is $C_1$–$C_4$ alkyl or $R^3CH_2$, wherein $R^3$ is $C_3$–$C_8$ cycloalkyl, $C_1$–$C_3$ haloalkyl, $C_1$–$C_3$ alkoxy, $C_1$–$C_3$ alkylthio, $C_1$–$C_3$ alkylsulfinyl, $C_1$–$C_3$ alkylsulfonyl, $C_1$–$C_3$ alkoxycarbonyl, cyano, amino, $C_1$–$C_3$ monoalkylamino, $C_1$–$C_3$ dialkylamino, $C_2$–$C_4$ alkenyl, $C_2$–$C_4$ haloalkenyl or $C_2$–$C_4$ alkynyl, $R^2$ is phenyl which may be substituted by halogen, $C_1$–$C_3$ alkyl, $C_1$–$C_4$ alkoxy, $C_2$–$C_4$ alkenyloxy, $C_2$–$C_4$ alkynyloxy, $C_1$–$C_4$ haloalkyl or $C_1$–$C_4$ haloalkoxy, $X^1$ is $C_1$–$C_4$ haloalkyl, $X^2$, $X^3$, $X^4$ and $X^5$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkyl-carbonylamino, and $r_1$ and $r_2$ are each independently hydrogen, halogen, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ together may form carbonyl.

5. Benzamidoxime derivatives according to claim 4, wherein $X^1$ is trifluoromethyl, and $r_1$, $r_2$ and $X^3$ are hydrogen.

* * * * *